US010940256B2

(12) United States Patent
Thiebaud et al.

(10) Patent No.: US 10,940,256 B2
(45) Date of Patent: Mar. 9, 2021

(54) HEMODIALYSIS SYSTEM

(71) Applicant: NextKidney SA, Lausanne (CH)

(72) Inventors: Pierre Thiebaud, Cressier (CH); Frédéric Neftel, Crans-Montana (CH)

(73) Assignee: NextKidney SA, Lausanne (CH)

( * ) Notice: Subject to any disclaimer, the term of this patent is extended or adjusted under 35 U.S.C. 154(b) by 0 days.

(21) Appl. No.: 16/785,678

(22) Filed: Feb. 10, 2020

(65) Prior Publication Data

US 2020/0171231 A1 Jun. 4, 2020

Related U.S. Application Data

(63) Continuation of application No. 15/305,675, filed as application No. PCT/IB2015/052995 on Apr. 24, 2015, now Pat. No. 10,596,309.

(30) Foreign Application Priority Data

Apr. 25, 2014 (WO) .................. PCT/IB2014/061006

(51) Int. Cl.
*A61M 1/16* (2006.01)
*A61M 1/28* (2006.01)
*A61M 1/34* (2006.01)
*B01D 61/30* (2006.01)

(52) U.S. Cl.
CPC ........ *A61M 1/1696* (2013.01); *A61M 1/1601* (2014.02); *A61M 1/1629* (2014.02); *A61M 1/1682* (2014.02); *A61M 1/1692* (2013.01); *A61M 1/287* (2013.01); *A61M 1/3472* (2013.01); *A61M 2205/3331* (2013.01); *A61M 2205/3337* (2013.01); *A61M 2205/3368* (2013.01); *A61M 2205/3393* (2013.01); *B01D 61/30* (2013.01); *B01D 2313/243* (2013.01)

(58) Field of Classification Search
CPC .............. A61M 1/1601; A61M 1/1629; A61M 1/1682; A61M 1/1692; A61M 1/1696; A61M 1/287; A61M 1/3472; A61M 2205/3331; A61M 2205/3337; A61M 2205/3368; A61M 2205/3393; B01D 2313/243; B01D 61/30
See application file for complete search history.

(56) References Cited

U.S. PATENT DOCUMENTS

| | | |
|---|---|---|
| 2010/0252490 A1 | 10/2010 | Fulkerson et al. |
| 2011/0272337 A1 | 11/2011 | Palmer |
| 2012/0022441 A1 | 1/2012 | Kelly et al. |
| 2012/0085707 A1 | 4/2012 | Beiriger |
| 2013/0213891 A1 | 8/2013 | Karoor |
| 2013/0220907 A1 | 8/2013 | Fulkerson et al. |
| 2015/0114891 A1 | 4/2015 | Meyer et al. |

FOREIGN PATENT DOCUMENTS

GB 2 124 511 A 2/1984

OTHER PUBLICATIONS

International Search Report (ISR) of the parent application PCT/IB2015/052995 dated Aug. 3, 2015.
Written Opinion of the International Search Authority of the parent application PCT/IB2015/052995 dated Aug. 3, 2015.

*Primary Examiner* — Terry K Cecil
(74) *Attorney, Agent, or Firm* — Andre Roland S.A.; Nikolaus Schibli

(57) ABSTRACT

A dialysis system comprises a filtration means, a pump and a sorbent device for performing a dialysis treatment and/or for regenerating a dialysate solution.

11 Claims, 10 Drawing Sheets

HEMODIALYSIS SYSTEM

CROSS REFERENCE TO RELATED APPLICATIONS

Figure 1:
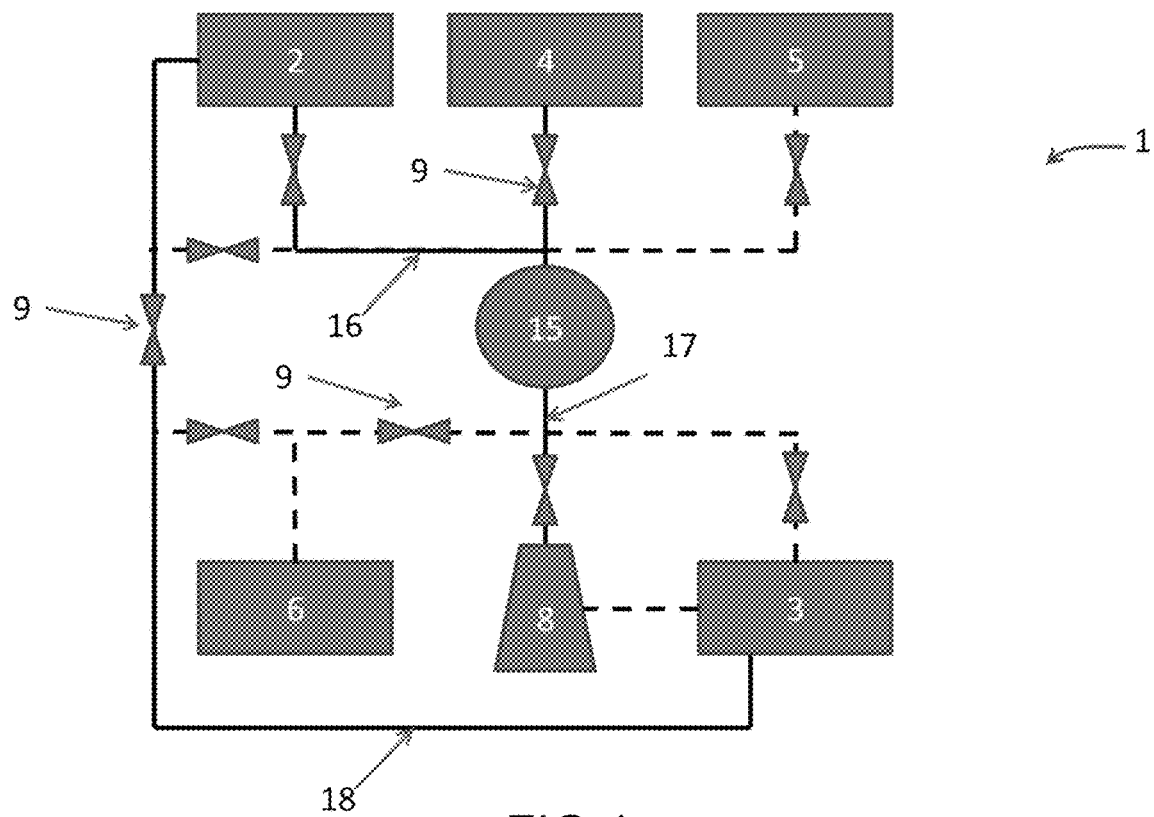

The present patent application is continuation application of U.S. application Ser. No. 15/305,675, now U.S. Pat. No. 10,596,309, that was filed on Oct. 21, 2016, which in turn is a U.S. national stage application of PCT/IB2015/052995 that was filed on Apr. 24, 2015 designating the United States, and claims foreign priority to International patent application PCT/IB2014/061006 that was filed on Apr. 25, 2014, the contents of both documents being herewith incorporated by reference in their entirety.

FIELD OF INVENTION

This invention is in the field of medical instruments for processing body fluids including an instrument to perform hemodialysis treatment or peritoneal dialysis.

STATE OF THE ART

Currently, the most widely used method of kidney dialysis for treatment of end stage renal disease is hemodialysis. In hemodialysis, the patient's blood is cleansed by passing it through a filtration means (for instance a dialyzer) and the treatment may be controlled by a dialysis machine. During dialysis, venous and arterial parts of blood line convey a patient's blood to and from the filtration means. Impurities and toxins are removed from the patient's blood by diffusion or convection across a membrane in the filtration means. Hemodialysis is generally required three times a week with each dialysis requiring four to five hours in a dialysis center or at home. During the treatment, the patient is connected to a hemodialysis machine and the patient's blood is pumped through the machine. Catheters are inserted into the patient's veins and arteries so that blood can flow to and from the hemodialysis machine. A large amount of a dialysis solution, for example about 120 liters, is consumed to dialyze the blood during a single hemodialysis therapy.

Peritoneal dialysis, although used less frequently than hemodialysis, is an accepted method for treating end stage renal disease. It is becoming increasingly a more popular form of dialysis. In peritoneal dialysis, a dialysis solution is infused into a patient's peritoneal cavity using tubing and a catheter. The peritoneum, which defines the peritoneal cavity, is composed of a membrane that contains many small blood vessels and capillary beds, in such a way that the peritoneal membrane acts as a filtration means. Peritoneal dialysis uses a dialysis solution or "dialysate", which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysis solution due to diffusion and osmosis, i.e., an osmotic gradient occurs across the membrane. The spent dialysate is drained from the patient, removing waste, toxins and excess water from the patient. This cycle is repeated and uses also a large amount of a dialysis solution.

The peritoneal cavity may be compared to the filtration means used in hemodialysis. Indeed, in both cases, impurities and toxins in the blood are removed across a filtration means. Hemodialysis and peritoneal dialysis are two types of dialysis therapies used commonly to treat loss of kidney function. Although dialysis equipment for home use is available, a patient must still remain relatively immobile during the course of treatment due to the non-portable nature of such dialysis equipment. Typical home-dialysis equipment employs an amount of dialysis fluid greater than 20 liters and typically up to 120 to 200 liters. Thus the patient has to store at home a large volume of fresh dialysate and the patient hands several dialysate bags (fresh and spent) every day for treatment. Other machines allow transforming water into dialysis solution but these machines use a large amount of energy and water, while representing a potential contamination risk. In both cases, the environmental impact is important. Another drawback of these dialysis systems using the water is the need for a dedicated water treatment, which includes equipment, water connection and drainage. Installing and using those components is a difficult and cumbersome task that can require a patient's home to be modified.

The large volume of dialysate required for dialysis is in part attributable to the large quantity of solution necessary for the diffusion of waste products removed and the balancing of electrolytes within the dialysate from the blood of a dialysis patient. Regeneration of spent dialysate is one way to reduce the total volume of a dialysis system by eliminating the need for a large reserve of fresh dialysate. In order for spent dialysate to be reused, accumulated waste products and impurities must be removed from the spent dialysate, and the composition and pH of the regenerated dialysate must be regulated for physiological compatibility. Devices that regenerate spent dialysis fluid are primarily directed toward the removal of urea, ammonium ions, uric acid, creatinine, and phosphate via various sorbents. For example, the Recirculating Dialysate System ("REDY system"), which was introduced in the 1970s, employs a sorbent cartridge through which spent dialysate is recirculated and regenerated. However, the regenerated dialysate produced by REDY systems is subject to variations in pH and sodium concentrations and therefore become non-conducive to physiological norms.

The most recent machines can regenerated a dialysis solution and injects—via a dedicated pump and/or dedicated device—sodium or other components into the dialysis solution which has flowed through the sorbent. One of drawbacks of these machines is the use of a specific device or pump, so that the machines are complex, expensive and comprise several elements which use energy. Furthermore, this type of machine is large, expensive and heavy, making it inappropriate to use at home and for patient transportation.

GENERAL DESCRIPTION OF THE INVENTION

All mentioned drawbacks may be obviated by the device for dialysis system according to the invention.

One of goals is to have a dialysis system which has a size and weight suitable to be used at home while enabling transportation. Said dialysis system may comprise a regeneration system which is at least in part incorporated into a dialysate circuit in such a way as to simplify the dialysis system, while limiting the elements needed to regenerate a dialysis solution at lower cost. For example, the dialysis system may comprise a filtration means and a sorbent device configured to allow dialysis solution to pass through. The filtration means is adapted to remove one or more substances contained into the blood of a patient. The sorbent device is adapted to remove one or more substances contained into a dialysis solution. Preferentially, the system is a loop circuit in which the dialysis solution passes through. Said loop circuit of the dialysate may be a closed loop circuit in which the system can inject additional solution, for example, fresh dialysate, regeneration solution, . . . . Thus, a dialysis solution kept in a bag may first flow through said filtration means then may reach said sorbent device and may come back to the bag.

In a first aspect of the invention, the bag is a mixing bag in which a dialysis solution is stored. The dialysate solution in the mixing bag changes over time during the treatment and may need to be blended with another solution (fresh dialysate or concentrate solution) in the mixing bag. Said system may comprise only one scale means (for instance one scale or two redundant scales) designed in such a manner as to monitor the treatment. In particular, said scale may be adapted to only monitor the volume or the weight of the fluid stored in the mixing bag.

In a second aspect of the invention, a dialysis system comprises a cassette comprising channels and a pump which may be used by a dialysis solution and a regeneration solution (also called concentrate solution) in such a way as to simplify the fluid pathway and limited the number of pumps. Thanks to this design, the system may use a method for regenerating a dialysis solution using a same pumping means for conveying all or part of a dialysis solution as well as a regeneration solution.

In a third aspect of the invention, the dialysis system comprises at least one bypass in such a way as to bypass the sorbent device and/or the filtration means. The bypass is particularly useful when a solution does not need to flow through the sorbent device or the filtration means. For example when a regeneration solution is conveyed to the mixing bag, said regeneration solution does not have to pass through the sorbent device. Indeed, if the regeneration solution passed through the sorbent device, said regeneration solution could be affected. Thus, if the regeneration solution passes through the dialysate circuit, said dialysate circuit has to comprise a bypass means to bypass the sorbent device.

In other cases, a bypass may be used as a security means, for instance to convey a used dialysis solution—which is not good to use—through another pathway rather through a filtration means. It may also be useful, for example, if the dialysis solution is too hot or too cold, or non-conducive according to physiological norms. Thus, the dialysis solution may pass one more time through the dialysis machine or convey to a bag (waste bag or mixing bag) without flowing through the dialyzer.

In a fourth aspect of the invention, a dialysis system comprises only one pumping means (for instance only one pump, e.g. peristaltic pump, . . . ) for moving the dialysis solution through the dialysate circuit. Thus, said pumping means is adapted to convey (push) the dialysis solution to the dialyzer and/or to remove (pull) the dialysis solution from the dialyzer. For instance, the pump may be adapted to move a dialysis solution from a bag to a dialyzer and/or from the dialyzer to the bag and trough a sorbent device.

In a fifth aspect of the invention, a dialysis system comprises two distinct pumping means for moving the dialysis solution through a dialysate circuit. A pumping means may be located upstream a filtration means (dialyzer) and an additional pumping means may be located between the filtration means and a sorbent device. Said system may be adapted to control the pumping means in order to favor a diffusive clearance or a convective clearance.

LIST OF FIGURES

Figure 2:
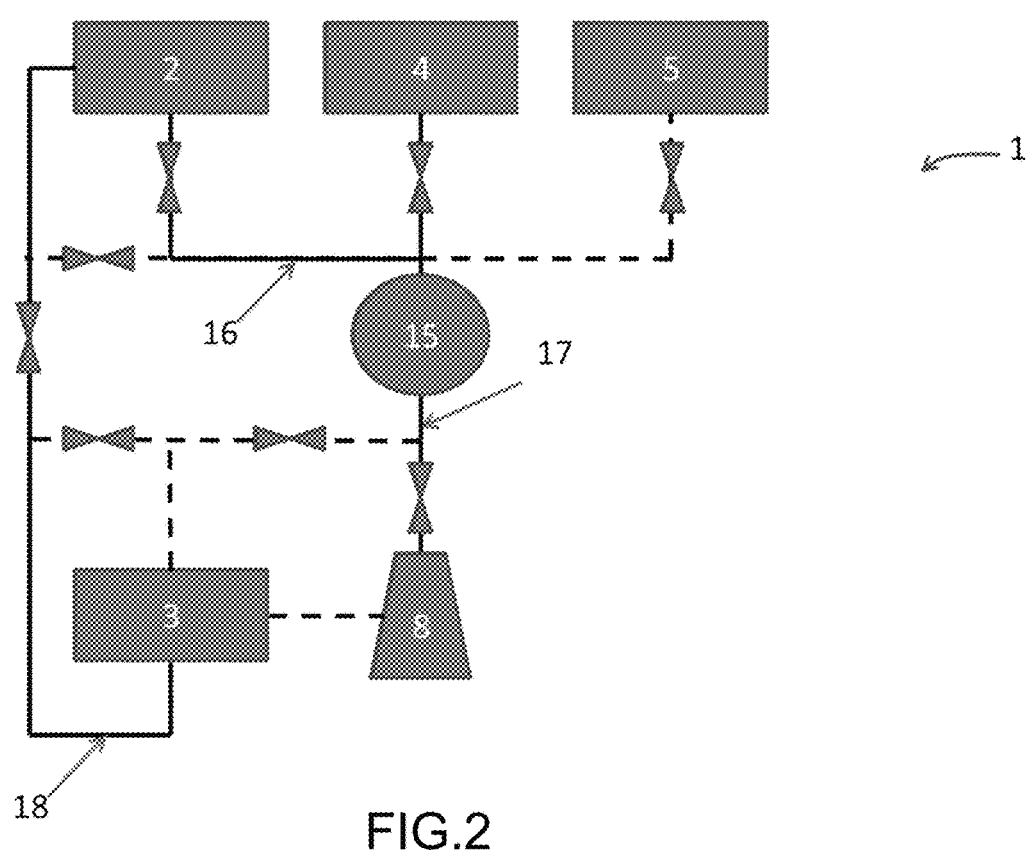
Figure 3:
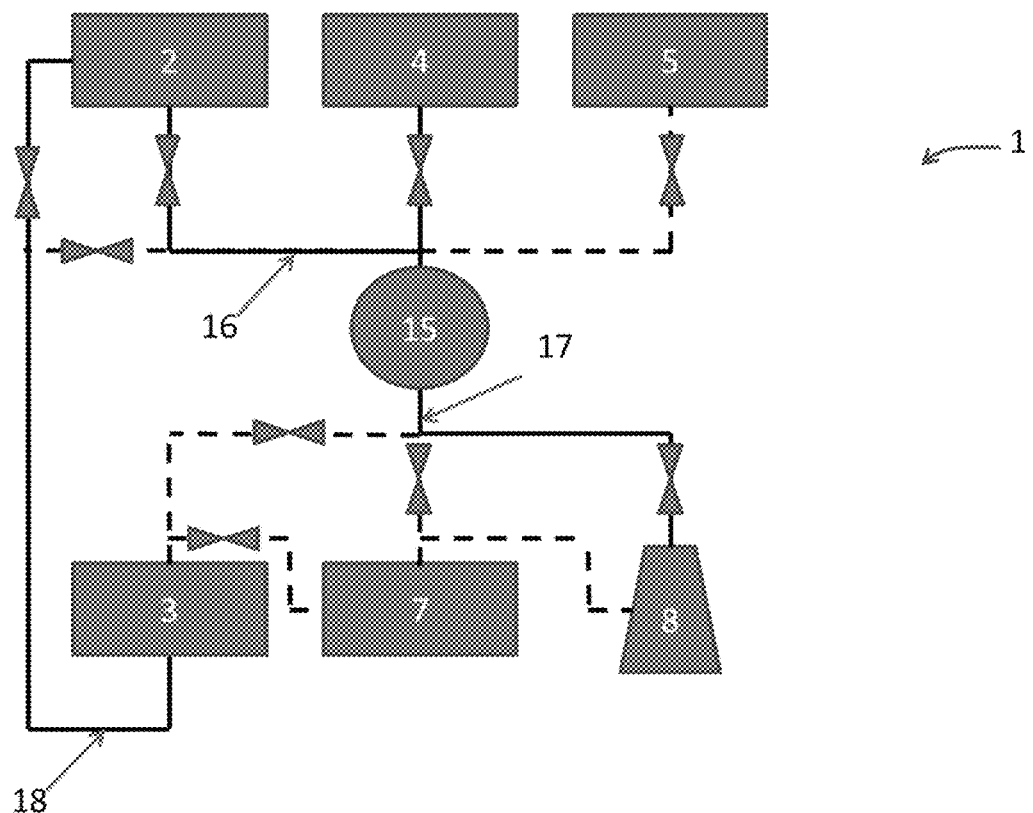
Figure 4:
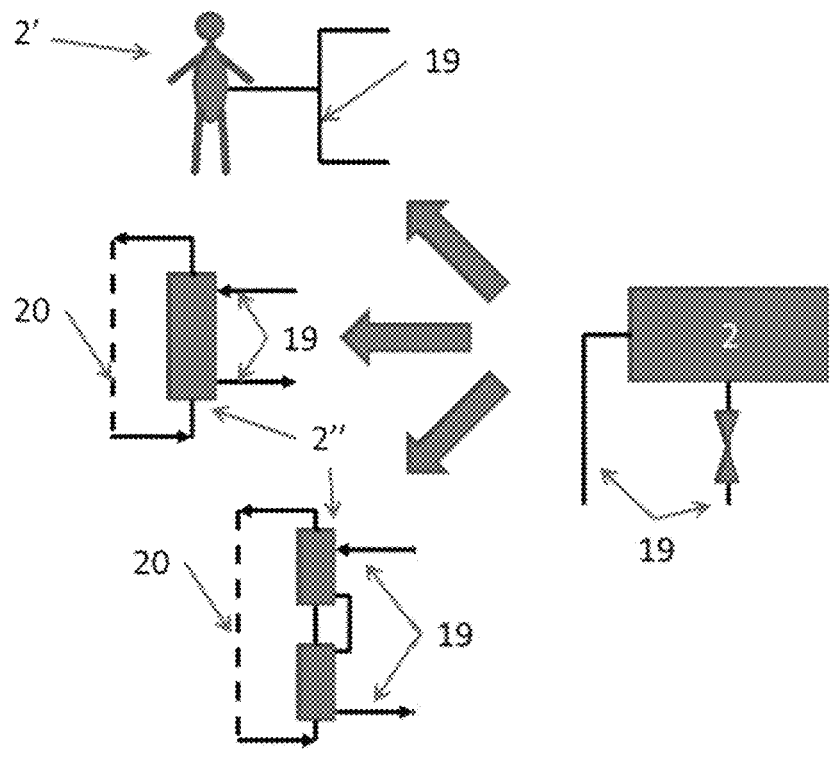
Figure 5:
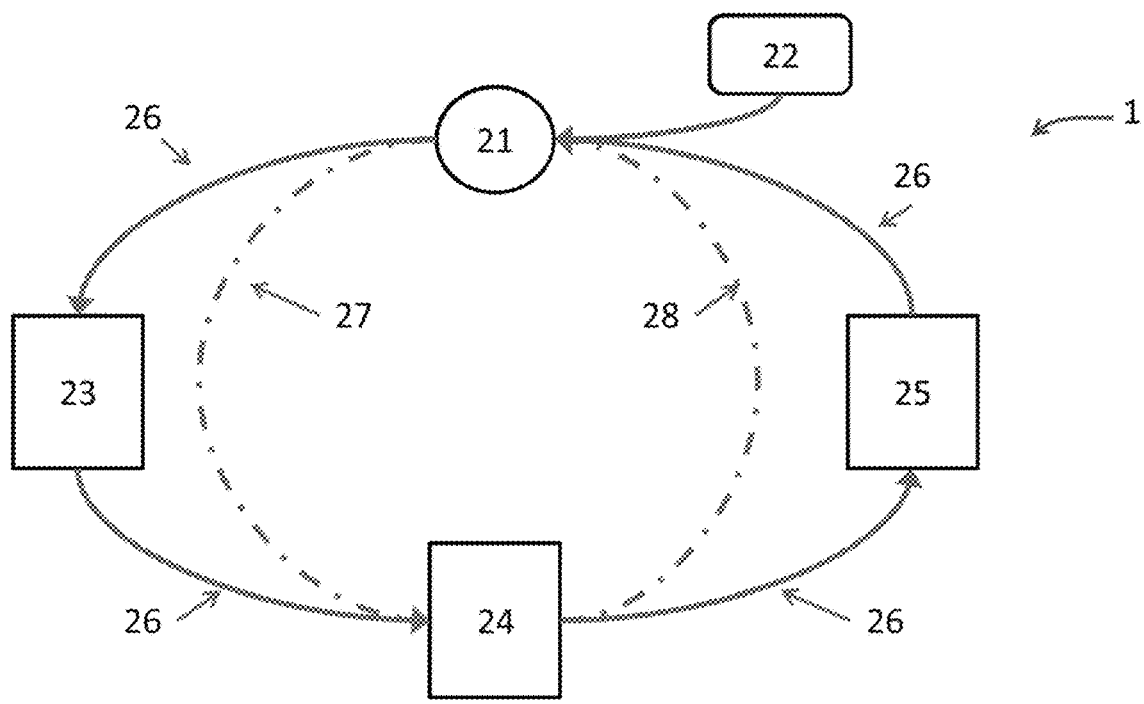
Figure 6:
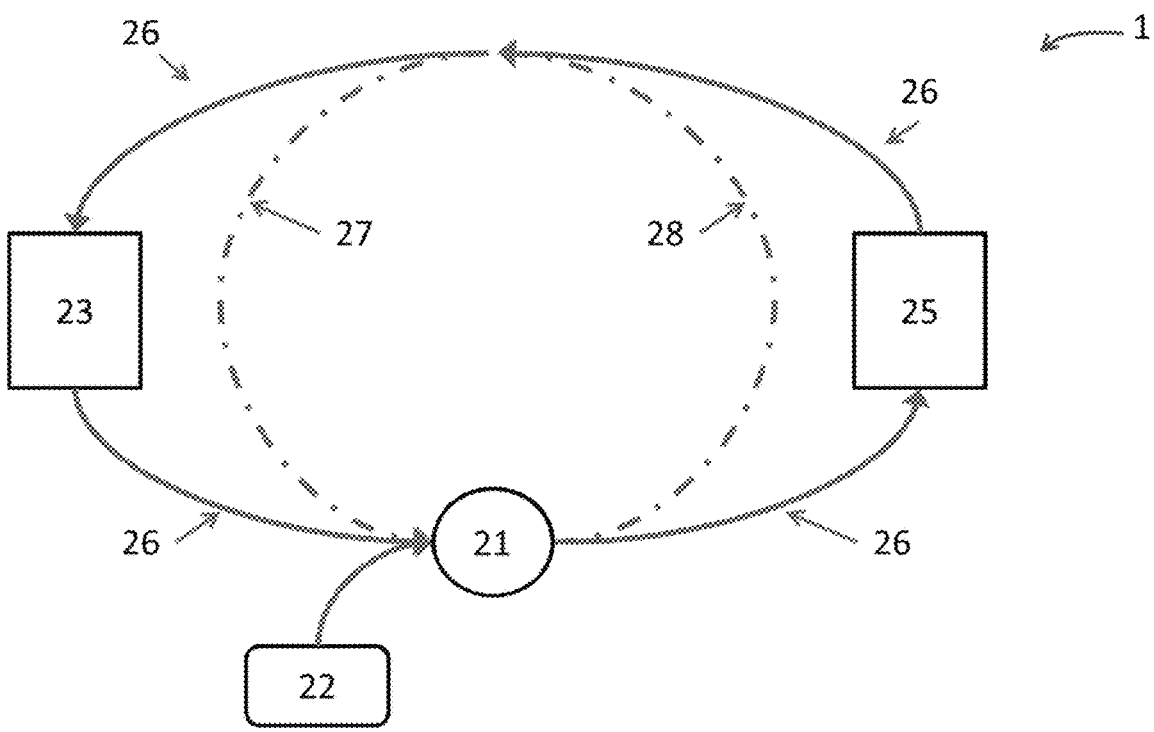
Figure 7:
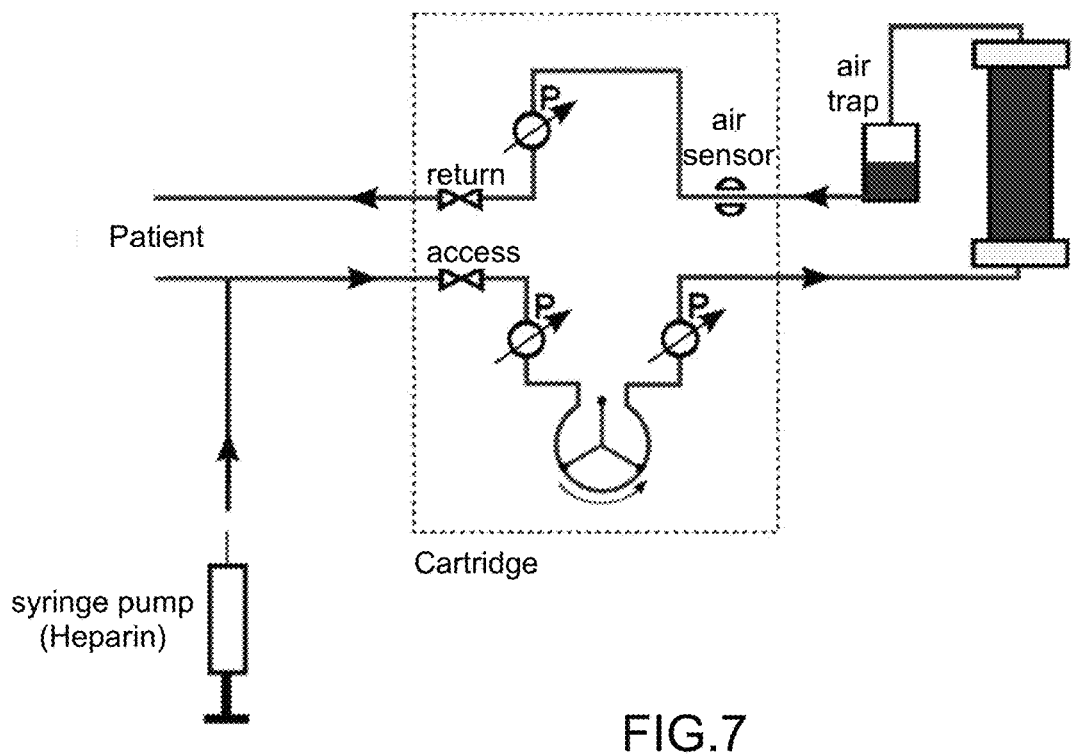
Figure 8:
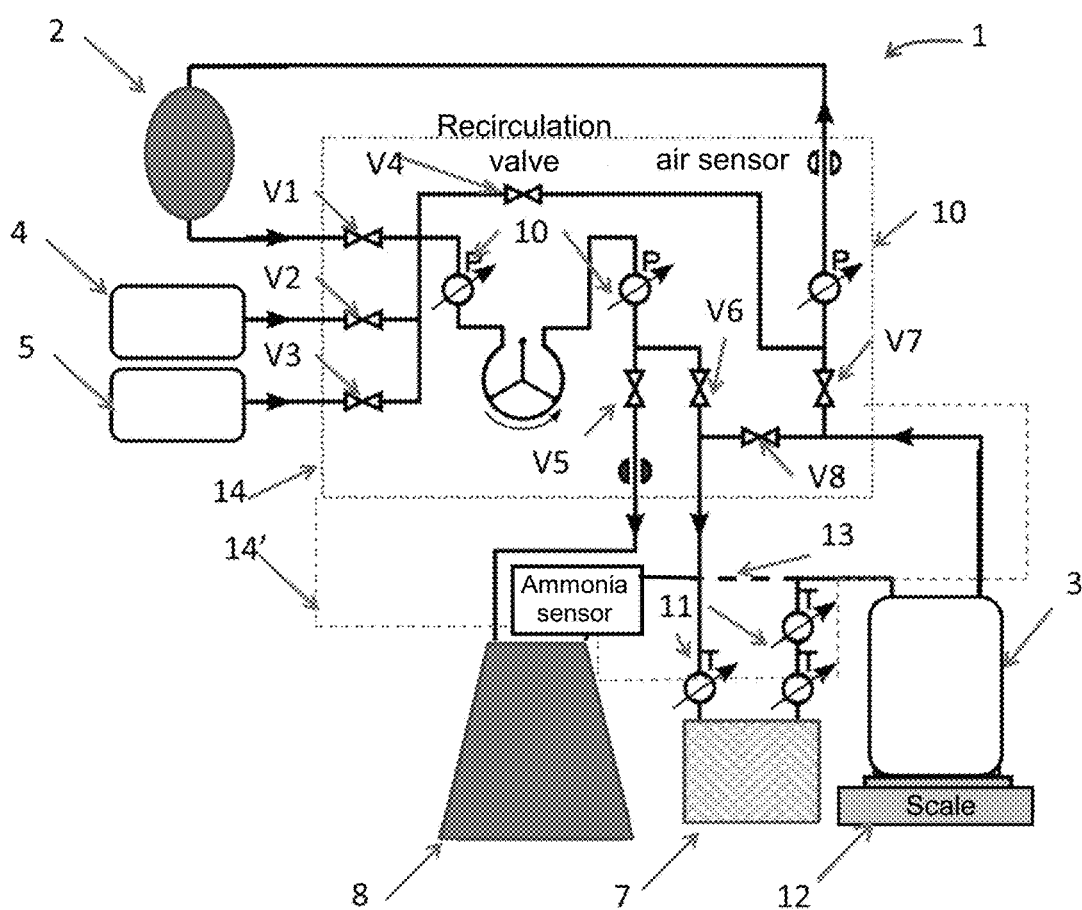
Figure 9:
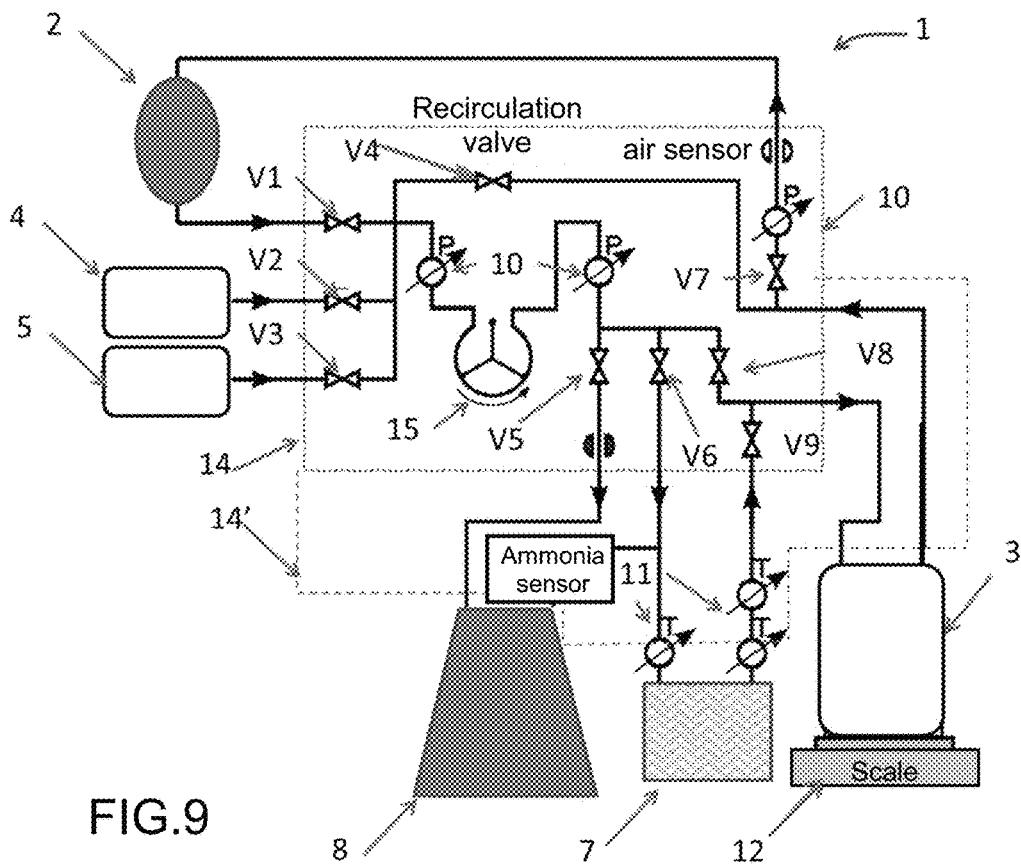
Figure 10:
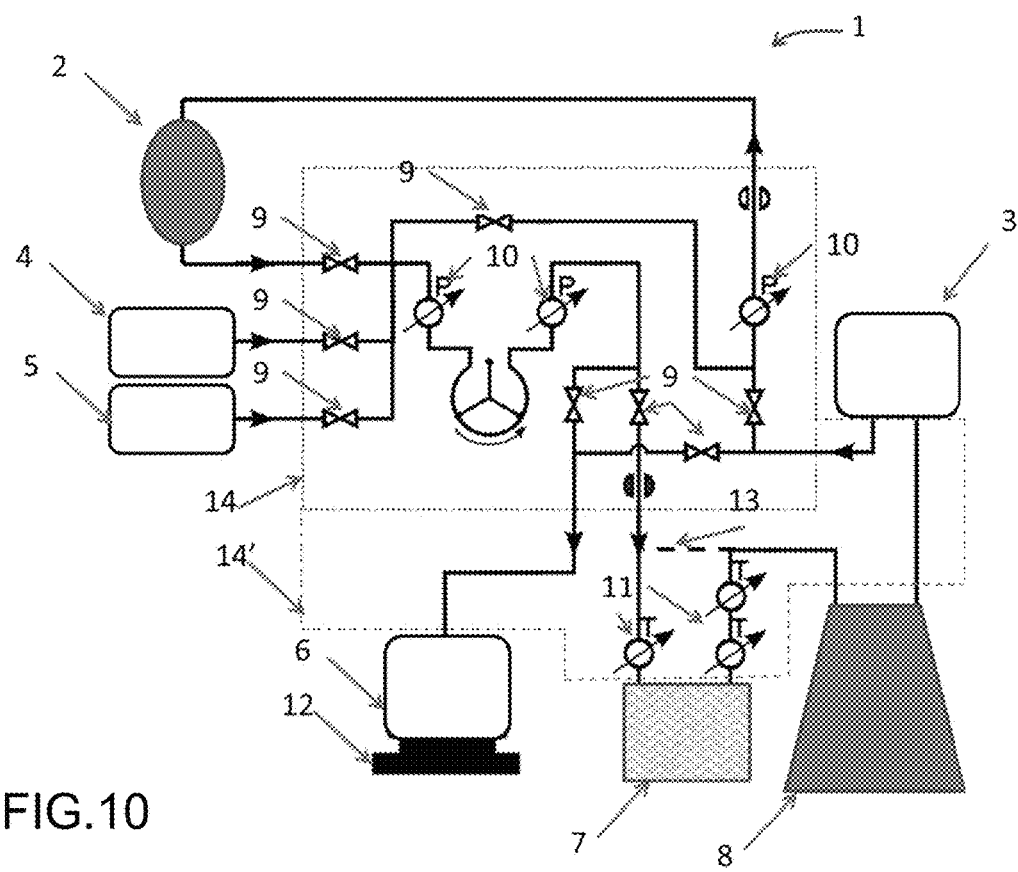
Figure 11:
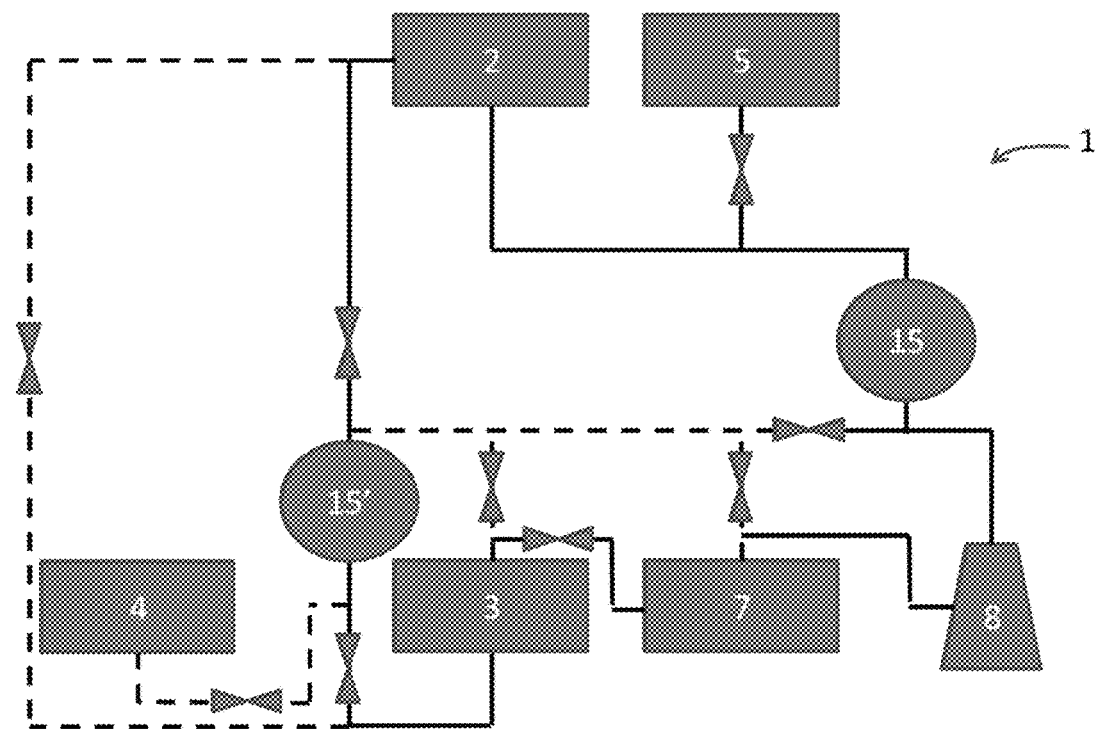
Figure 12:
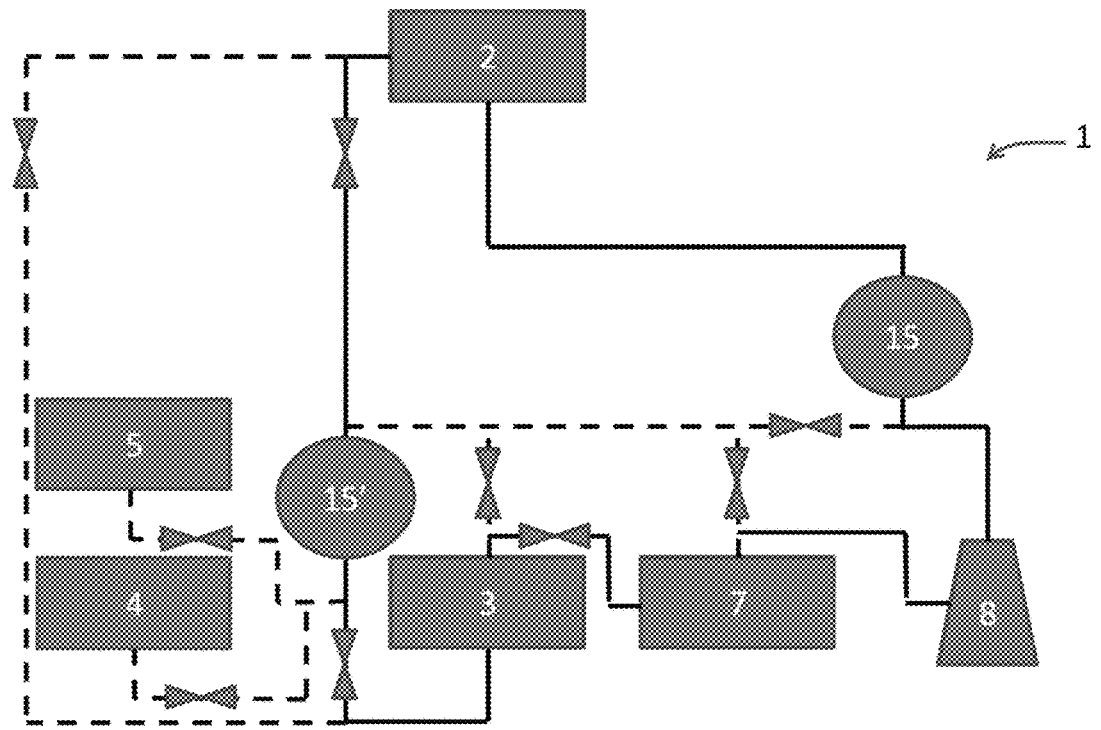
Figure 13:
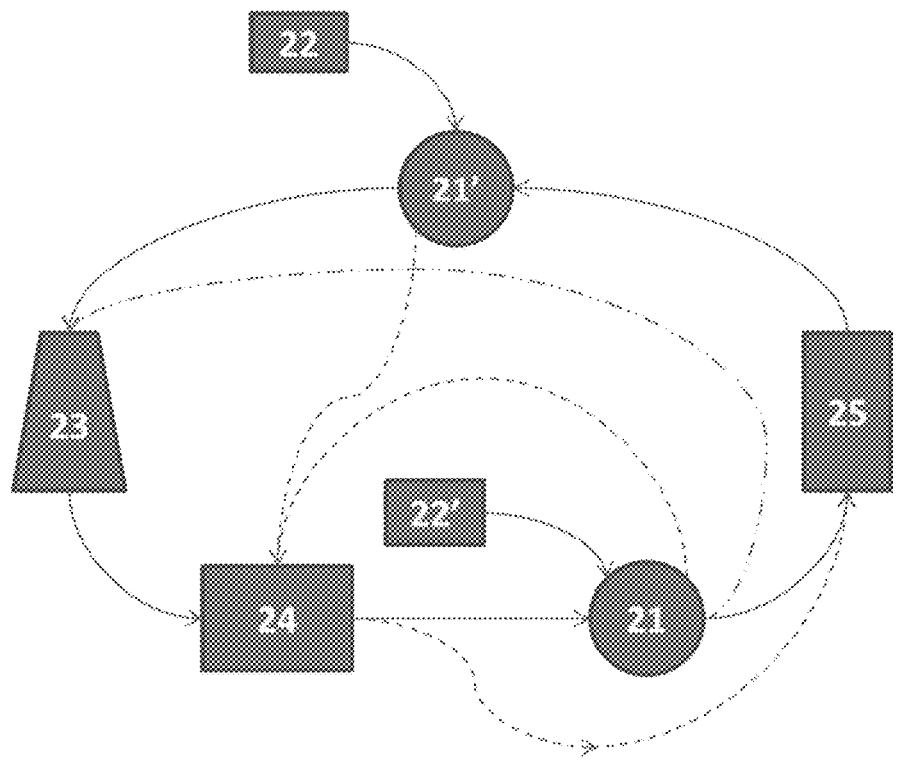
Figure 14:
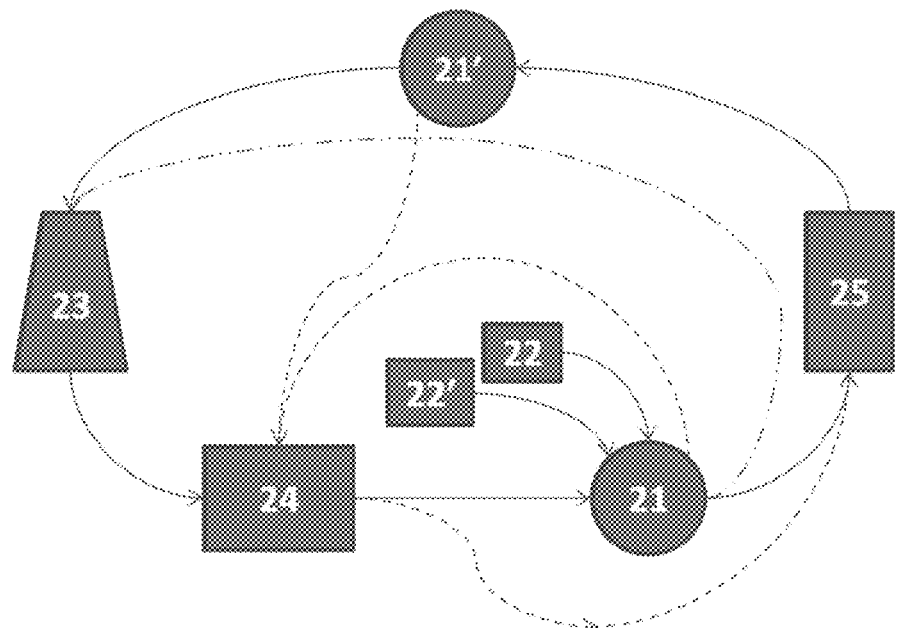
Figure 15:
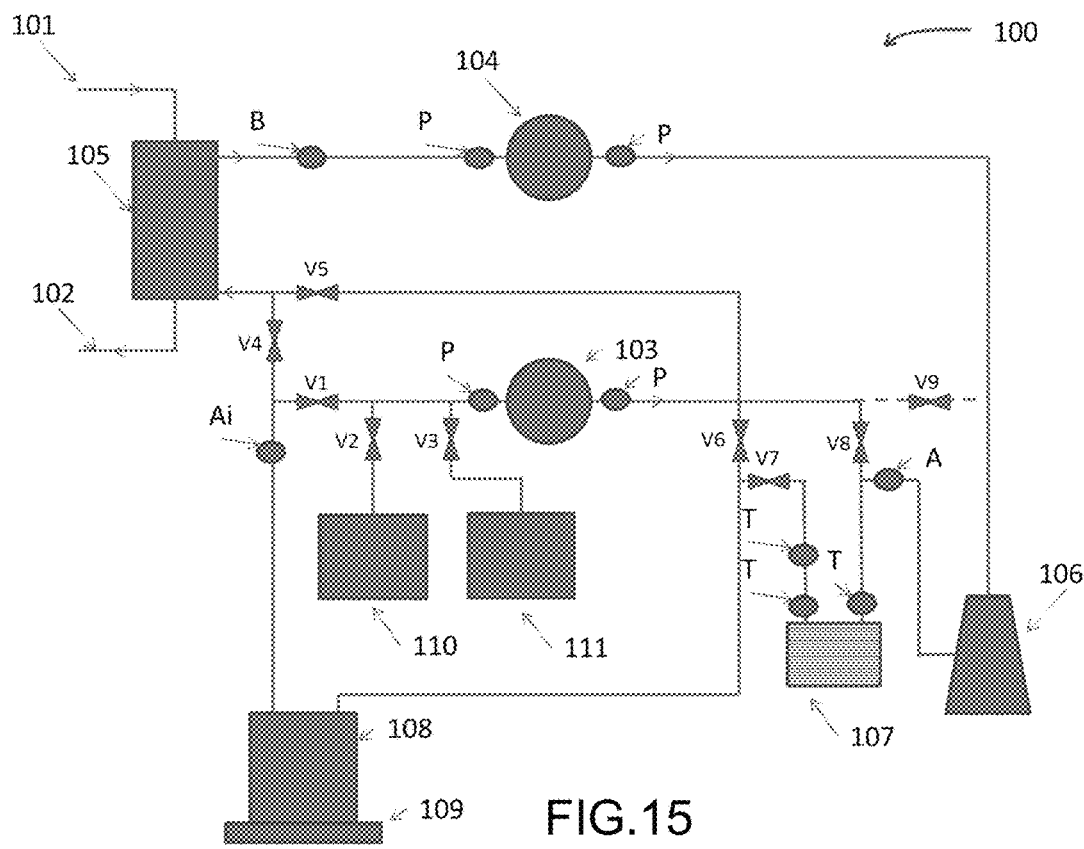
Figure 16:
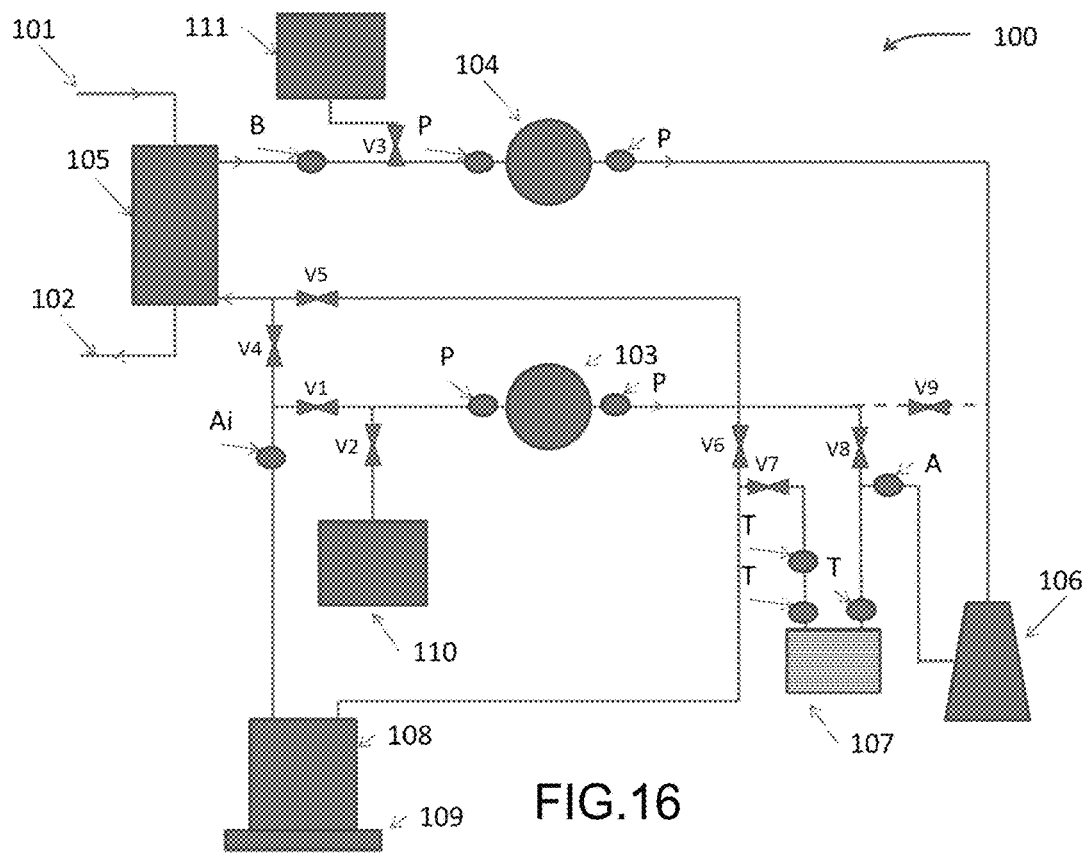
Figure 17:
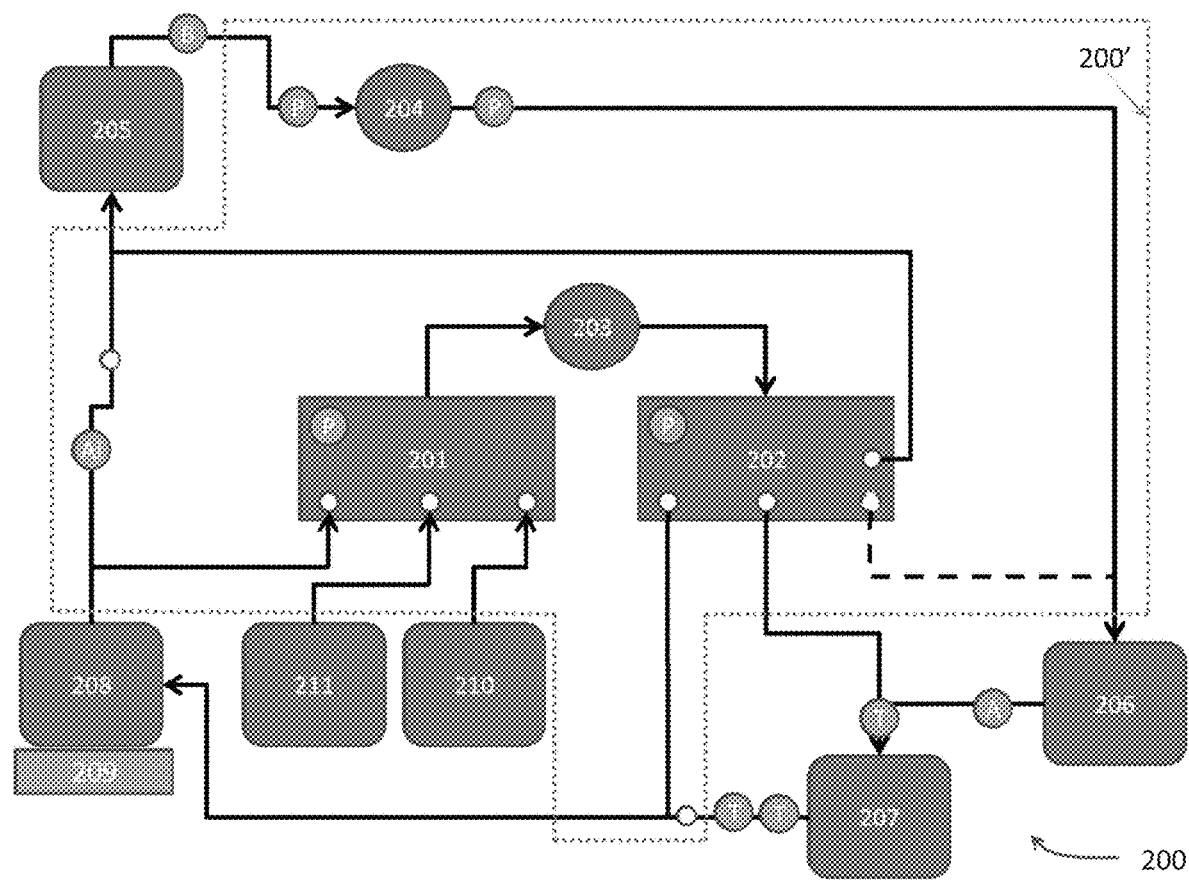

The present invention will be better understood at the light of the following detailed description which contains non-limiting examples illustrated by the following figures:

FIGS. 1, 2 and 3 show a schematic view of three distinct possible embodiments FIG. 4 illustrates the filtration means using only one pump FIGS. 5 and 6 shows a schematic view of two distinct possible dialysate circuits FIG. 7 shows a schematic view of a blood circuit FIGS. 8, 9 and 10 show a schematic view of three distinct possible embodiments FIGS. 11, 12 and 13 show a schematic view of three distinct possible embodiments using two distinct pumps FIGS. 13 and 14 shows a schematic view of two distinct possible dialysate circuits using two pumps FIGS. 15, 16 and 17 show a schematic view of three distinct possible embodiments using two distinct pumps.

Figure 18:
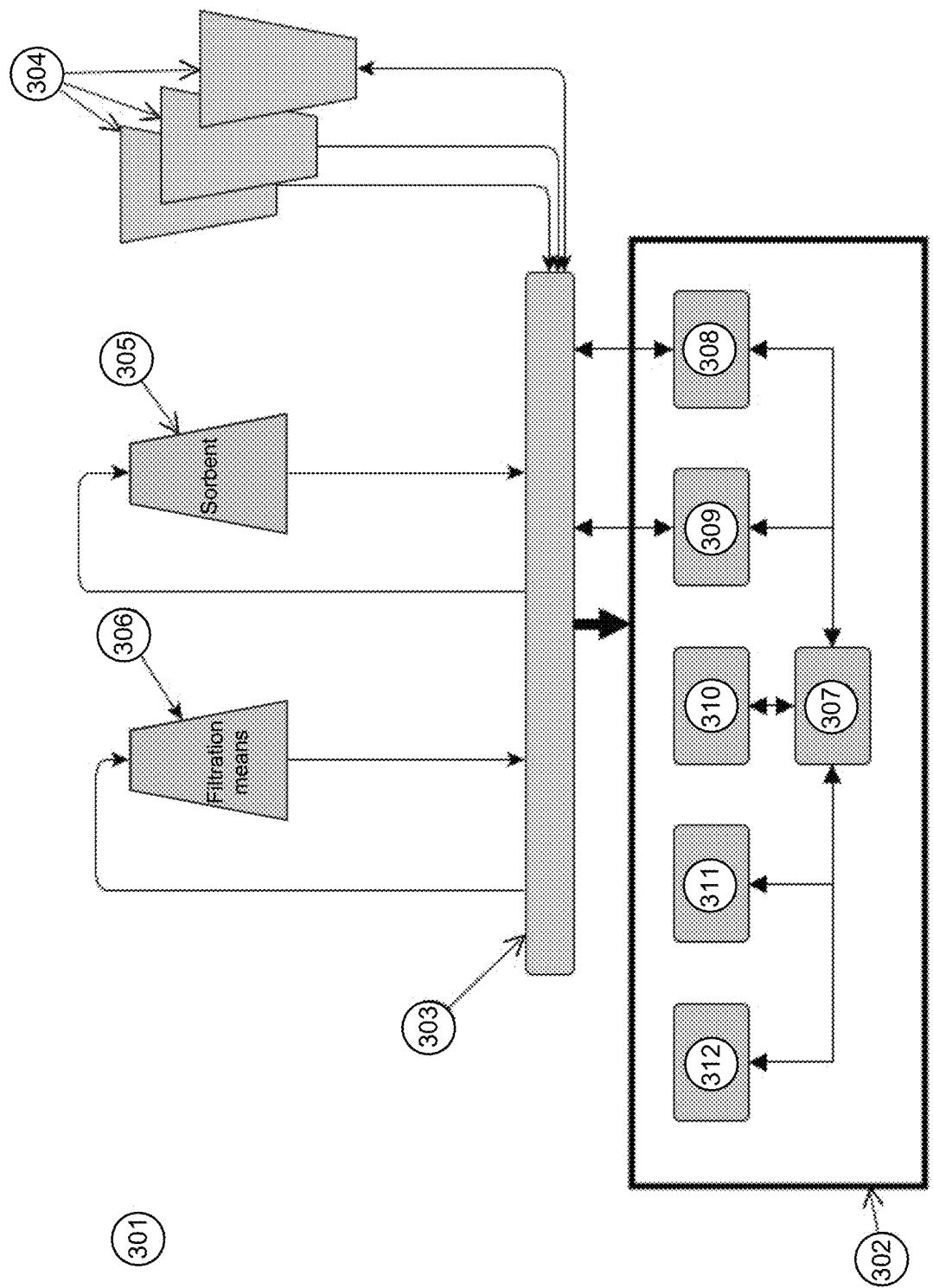

FIG. 18 shows a dialysis system.

LIST OF ELEMENTS

1 Fluid distribution system
2 Filtration means
2' Embodiment wherein the filtration means is a peritoneal cavity
2" Embodiment wherein the filtration means is a dialyzer or multi-dialyzers
3 Bag
4 Bag
5 Bag
6 Bag
7 Heater
8 Sorption unit
9 Valve
10 Pressure sensor
11 Temperature sensor
12 Scale
13 Channel
14, 14' Cassette
15, 15' Pumping means
16 First channel
17 Second channel
18 Third channel
19 Dialysate circuit
20 Other fluid circuit (Blood, . . . )
21, 21' Pump
22, 22' Supply bag
23 Sorbent device
24 Mixing bag
25 Filtration means
26 First line (main line)
27 Second line or first by-pass
28 Third line or second by-pass
30 Fluidic pathway in which a fluid flows from a filtration means to a pump
31 Fluidic pathway in which a fluid flows from a pump to a sorbent device
32 Fluidic pathway in which a fluid flows from a sorbent device to a reservoir
33 Fluidic pathway in which a fluid flows from a reservoir to a filtration means
40 Fluidic pathway in which a fluid flows from a pump to a filtration means
41 Fluidic pathway in which a fluid flows from a filtration means to a sorbent device
42 Fluidic pathway in which a fluid flows from a sorbent device to a reservoir
43 Fluidic pathway in which a fluid flows from a reservoir to a pump
50 Dializer 51 Sorbent device
52 Optional heater
53 Scale
54 Mixing bag
55 Additive bag
56 Dialysate flow
57 Blood line
58 Blood line
59 Cassette
V. Valve
S. Sensor
P. Pressure sensor
T. Temperature sensor
B. Blood sensor
A. Ammoniac sensor
Ai Air Sensor
100 Fluid distribution system
101 Inlet (blood circuit)
102 Outlet (blood circuit)
103, 104 Pump
105 Filtration means
106 Sorbent device
107 Heater means
108 Mixing bag
109 Scale
110 Regeneration supply bag
111 Dialysate supply bag
200 Fluid distribution system
200' Potential limit of the cassette
201 First chamber (channel)
202 Second chamber (channel)
203, 204 Pump
205 Filtration means
206 Sorbent device
207 Heater means
208 Mixing bag
209 Scale
210 Concentrate supply bag
211 Dialysate supply bag
301 Dialysis system
302 dialysis machine
303 Cassette
304 Bag
305 Sorbent device
306 Filtration means
307 Processor
308 Pumping means
309 Valve
310 Element electronically connected to the processor
311 Sensor
312 Scale

DETAILED DESCRIPTION OF THE INVENTION

The invention is set forth and characterized in the independent claims, while the dependent claims describe other characteristics of the invention.

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

The present application claims the benefit of the priority of PCT/IB2014/061006 filed on 25 Apr. 2014 in the name of Debiotech S. A., the entire disclosure of which is incorporated herein by reference.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to.

As used in this specification and the appended claims, the term "or" is generally employed in its sense including "and/or" unless the content clearly dictates otherwise.

As used herein, the term "cassette" refers to an element of a fluid distribution system. A cassette comprises a number of defined channels, valves and fluidic connection means. The fluidic connection means (also named connection port) are designed to make possible a fluidic connection between a channel of the cassette to an element which is located outside the cassette. For instance, a pumping means may be connected to at least one channel of the cassette, the inlet and outlet of the pumping means may cooperate with the cassette in such a way as to be in fluid communication with the channels of the cassette. Said pumping means may be outside the cassette and/or directly fixed against the cassette. In one another embodiment, the pumping means may be in the cassette. A fluidic connection means may extend externally from the cassette to an element via a tube or directly so that the fluidic connection means may rigidly fix the element to the cassette. In this document, a pump, a heater, a filtration means and/or a sorbent device may be connected or in fluid communication to the cassette via fluidic connection means.

The cassette may be a disposable element which cannot be reused after a single treatment. During the treatment, the cassette may be secured to a cassette holder of a dialysis machine of the dialysis system. The dialysis machine can be reused several times and reused with distinct cassettes. The fluid distribution system may include pumping means for moving the fluid through the dialysis system, sensor for monitoring the treatment and actuators for opening and closing valves or for actuating the pumping means. Thanks to the valve and the pumping means, the dialysis machine controls the fluid distribution system. The dialysis machine may be commanded by an electronic processor so that the treatment can be performed, at least in part, automatically.

As used herein, the term "channel" of a cassette refers to a fluid passageway which is arranged into the cassette.

As used herein, the term "fluidic pathway" refers to a fluid passageway which allows conveying a fluid from an element to another element.

In other terms, a fluid distribution system comprises a line in which a solution flows. Different elements (bag, pump, filtration means, heater . . . ) are in fluid communication through said line with, in-between each element, defines fluidic pathways. If the fluid distribution system comprises a cassette, then a fluidic pathway may pass through a channel of the cassette. Thus, a channel may be a part of a fluidic pathway, and a fluidic pathway and a channel are a part of the line.

Dialysis System

A dialysis system (301) is shown in the FIG. 18. Sais dialysis system may comprise a cassette (303), a dialysis machine (302), bags (304) (for example mixing bag, supply bag, waste bag, . . . ). The dialysis machine may comprise a processor (307) which may control pumping means (308) and valves (309) adapted to cooperate with the cassette (303). The processor may be connected to sensors arranged inside or outside the dialysis machine, said sensor may be a scale (312), other sensors (311) (e.g. pressure sensor, conductivity sensor, air sensor, . . . ) or other elements (310) electronically connected to the processor. The cassette may be in fluid communication with a sorbent device (as described in the PCT application WO 2009/157 877 A1 which is incorporated herein by reference) and/or a filtration means (306).

In case of hemodialysis treatment, the fluid distribution system comprises at least two distinct circuits which are the blood circuit and the dialysate circuit and some specific features for performing and monitoring the treatment.

In case of peritoneal dialysis treatment, the fluid distribution system does not comprise a blood circuit.

The Blood Circuit:

An example of a blood circuit is shown by the FIG. 7. The blood circuit comprises a single line in which the blood flows, a filtration means (a dialyzer) which divides in two part the line: venous part of line and arterial part of line. The blood circuit further comprises a pump which removes the blood of the patient by the arterial part of line, convey the blood trough filtration means (to remove impurity, water, . . . ) and re-injects the blood to the patient by the venous part of line. The blood circuit may comprise an infusion set which infuses a physiologic solution (saline) and/or an anticoagulant, such as heparin or sodium citrate and calcium, into the blood line. Typically, at least a part blood circuit is disposable, in particular, the elements, which have been in contact with the blood, have to be discarded after use.

During the treatment, a pump of the blood circuit is pumping continuously. An interruption of the blood flow increase the risk of blood clotting, therefore a continuous flow is recommended. The blood circuit may comprise two valves, (access and return) which remain opened during the treatment. For example, these valves can close in order to protect the patient in case of a risk (e.g. blood leak from the set or to avoid air injection). The blood circuit may comprise three sensors for monitoring the pressure: at the patient access, at the patient return and at the outlet of the pump before the filter if the blood is pumped through the filter at positive pressure (or at the inlet of the pump in case the blood is sucked from the filter at negative pressure). These sensors can detect abnormal pressures that can result from an occlusion or a bad connection. An air trap may be placed after the filter for collecting the air before the blood returns to the patient. If some air however escapes from the air trap, an air sensor detects it and the flow can be stopped before this air reaches the patient. The blood circuit may comprise an infusion set of anticoagulant (e.g. heparin) which may be placed as close as possible of the patient access. Alternatively, sodium citrate can also be injected as close as possible to the patient access, in order to prevent coagulation, in which event calcium will need to be injected in the blood flowing back to the patient after the filter to neutralize the citrate anti-coagulation effect.

The Dialysate Circuit:

The FIGS. 1, 2, 3, 11 and 12 show schematic views of different embodiments of the dialysate circuit. The dialysate circuit comprises at least one valve (9) and at least one pump (15). In particular, the FIGS. 1, 2 and 3 show a dialysate circuit comprising only one pump while the FIGS. 11 and 12 show a dialysate circuit comprising two distinct pumps. The fluid distribution system includes at least one bag (3, 4, 5, 6) which may comprise:

a dialysis solution:
 fresh (i.e. new dialysate ready for the treatment), or
 spent (i.e. a dialysate which is already used, for instance after having passed through the filtration means), or
 regenerated (i.e. a spent dialysate which has flowed through a sorption unit blended, or not, with a regeneration solution), or
a regeneration solution (also called concentrate solution), or
other solution (e.g. heparin, . . . ).

Said dialysate circuit is connected to a filtration means (2). As showed in FIG. 4, said filtration means may be a peritoneal cavity of a patient (2') (if the treatment is a peritoneal dialysis) or a dialyzer (2") (single or multi dialyzer) for performing a hemodialysis treatment (for instance). Multiple dialyzers may be used for different purposes (e.g. one dialyzer for blood purification, one for toxin adsorbtion, one for oxygenation, etc . . . ).

The dialysate circuit further comprises a sorbent device and the dialysate circuit is adapted to:

pass a dialysate solution through the filtration means (so that remove impurity, water, waste (etc.) from the blood of patient), remove the spent dialysate solution from the filtration means, pass the spent dialysate solution through the sorbent device (to remove from the spent dialysate solution the impurities, waste . . . ).

This circuit is a loop circuit. Thanks to this circuit, a dialysate solution can be reused several times at least during one multiple hours treatment.

Nevertheless, the drawback of a sorbent device is that it removes too much components of the dialysate solution (for instance calcium, magnesium, . . . ) which makes the dialysate solution non ideal for use through further cycles. Therefore, a regeneration solution (also named concentrate solution) has to be injected into the dialysate circuit to regenerate a dialysate solution which can be used again for the treatment. Typically the regeneration solution may contain Calcium, Magnesium and/or other components which may be necessary to regenerate a dialysate solution (for example to obtain a dialysate solution comprising substantially a same composition than a fresh dialysate). Said regeneration solution may contain all or part of the components of a fresh dialysate and said components may be more concentrated than the components of standard fresh dialysate. Said regeneration solution may contain some components which have been removed by the sorbent device. The use of a conductivity sensor helps ensuring the proper electrical conductivity of the solution, such conductivity being representative of the mixing.

Mixing Bag

Preferentially, the dialysate circuit comprises a mixing bag. Said mixing bag is arranged in the loop circuit of the dialysate solution.

In one embodiment, during the treatment, a dialysate pump continuously removes a volume fraction of the dialysate solution from the mixing bag which will be used for the treatment. When the dialysate solution comes back to the mixing bag said solution is not optimal for the treatment and may be blended with the solution not used (which has been kept in the mixing bag) during the use. Thus, the dialysate solution changes over time during the treatment.

During the treatment, the chemical properties of the dialysate solution may be monitored by a conductivity sensor. If said properties reach a threshold, the system may automatically regenerate the dialysate solution and inject a volume fraction of regeneration solution in the mixing bag.

During the treatment, the volume of the solution can increase due to the ultrafiltration. The system may comprise a scale so as to monitor the ultrafiltration (the amount of the ultrafiltrate removed during the treatment). This scale may be an electronic balance (or two redundant electronic balances) which weighs the mixing bag, in particular this scale is adapted to monitor the volume of the fluid contained in the mixing bag. An electronic processor receives the data of the balance so as to determine the amount of the ultrafiltrate for example at any time during the treatment. Said scale may be used for determined the volume fraction of a regeneration solution injected during a regeneration phase.

The mixing bag may be used to trap the air which flows in the dialysate circuit. The mixing bag may be a flexible punch. Thus, with an adequate arrangement of the tubes or channels, the mixing bag (3) can serve as a means for accumulating any amount of circulating air (including the air coming from the priming). In this case, the mixing bag may comprise an outlet which is always in fluid communication with the dialysate solution contained in the mixing bag, for example a tube comprising an open fully immersed in the dialysate solution (contained in the mixing bag). If some air escapes from the bag because, for instance, when not enough dialysate is present inside the bag, the air sensor placed after the bag can detect it. And the system is adapted to close and open some valves so as to guide the air into a bag or into the mixing bag without passing by the filtration means (2).

The advantage of using a sorbent unit and a mixing bag is particularly interesting since only a small amount of fluid is needed (e.g. 5 liters instead of 60 to 120 liters).

Bypass Means

The FIGS. 5, 6, 13 and 14 show a schematic view of this loop of the dialysate circuit. The fluid distribution system comprises a dialysate circuit in which the pump (21) conveys a dialysate solution through a main line, which may be called first line (26). The dialysate solution passes through a filtration means (25) and then through a sorbent device (23). The fluid distribution system comprises at least one bag (22, 24) for storing a dialysate solution, a regeneration solution or a priming solution. Preferentially, the fluid distribution system comprises a supply bag in which is stored a regeneration solution (22') or a dialysate solution (22). The fluid distribution system (1) is adapted to use the same pump (21) for conveying the dialysate solution through a loop circuit and the regeneration solution from the supply bag (22) to the dialysate circuit.

A least one pump (21, 21') is located between the filtration means (25) and the sorbent device (23). The dialysate circuit may comprise two distinct pumps (21, 21') as shown by the FIGS. 13 and 14.

A part of the dialysate circuit may be arranged into a cassette and at least a part of the bypass is arranged into the cassette.

The supply bag (22) may contain regeneration solution or fresh dialysate.

As explained above, preferentially, a mixing bag (24) is a bag arranged in the loop circuit and in which a dialysate solution may be blended with another solution (for instance a regeneration solution), but in some cases, the dialysate circuit can also be used without this mixing bag.

The dialysate circuit may comprise a second line (27) (so named first bypass) adapted to bypass the sorbent device. Thus, a solution can:

flow through the sorbent device (23) or be temporarily derivate from the main line and reach the main line (26) after the sorbent device (directly the mixing bag (24)) so that the solution does not pass through the sorbent device (23).

The dialysate circuit may comprise a third line (28) (so named second by-pass) adapted to bypass the filtration means. Thus, a solution can:

flow through the filtration means (25) or be temporarily derivate from the main line and reach the main line (26) after the filtration means so that the solution does not pass through the filtration means (25).

It's particularly useful for different reasons, for instance, if the solution is too hoot or not good to used, this solution may be deviated from the filtration means. Furthermore, if a regeneration solution is not homogeneously blended with a dialysis solution, the second by-pass may be used to improve the mixing.

Other bypass means may be arranged into the dialysate circuit. As shown by the FIGS. 13 and 14, the main line is represented by a full line. This full line is a loop circuit (which may be considered as a closed loop circuit) in which the dialysate flows mainly. Thus, a dialysate solution successively pass through the first pump (21), the filtration means (25), the second pump (21'), the sorbent device (23) and reach the mixing bag (24). A first bypass may allow bypassing the sorbent device, thus the fluid flows from the second pump to the mixing bag. A second bypass may allow bypassing the filtration means (25) and the second pump (21') thus the fluid flows from the first pump to the sorbent device. A third bypass may allow bypassing the filtration means (25), the second pump (21') and the sorbent device (23) thus the fluid flows from the first pump to the mixing bag. A fourth bypass may allow bypassing the first pump thus the fluid flows from the mixing bag to the filtration means, said fluid being moved by the second pump. Thanks to the fourth bypass, when a dialysate solution flows from the mixing bag to the filtration means (without passing by the first pump), in a same time, another fluid (for instance the regeneration solution) may be moved by the first pump so as to be blended into the mixing bag with the dialysate solution.

Dialysis Machine and Cassette

In a preferred embodiment, a dialysate solution flow through a fluid distribution system (1) comprising a machine and a cassette adapted to cooperate there between. The machine comprises actuators design to actuate pumping means (15) and valves (9), in such a way as to convey a dialysis solution from point "A" to point "B". Said machine further comprises an electronic processor so as to control automatically all or particular valves and pumping means to perform automatically the treatment without help from a patient. It's particularly useful when the treatment is performed at home. The cassette comprises at least one valve and several channels. The valve is adapted to convey the dialysate solution in a specific fluid passageway, for example through a bypass or the main line, . . . .

Controller

The controller is adapted to monitor the treatment via different sensors: air sensor, blood sensor, ammonia sensor, pressure sensor, conductivity sensor, scale (balance) . . . . The controller controls the pumping means (velocity, . . . ), the valve(s), . . . and it is adapted to command the actuator depending on the dialysate solution and/or the treatment.

For example, if the dialysis solution has been passed through the filtration means, the controller may command to convey this solution through the sorbent device (23) before to reach the mixing bag (24) and/or the filtration means (25). When the pumping means move a regeneration solution, the controller may command the actuators in such a way that this solution can reach the mixing bag without passing through the filtration means and/or the sorbent device. If the dialysis solution cannot be used for the treatment, the controller may command the actuator so as to bypass the filtration means (25).

A rupture of the fibers inside the filtration means may also be considered. In this case some blood will enter in the dialysate fluidic pathway and a blood sensor may be placed in the dialysate circuit (for example before or after the pump) so as to detect this failure (e.g. a colour sensor).

An ammonia sensor may be placed after the sorbent device to control the proper functioning of the sorbent device. In the event the sorbent device is exhausted and cannot filter dialysate anymore it will release ammonia. This sensor can therefore also be used in order to detect the end of use of the sorbent unit.

A conductivity sensor may be arranged in the dialysate circuit for example into or after the mixing bag (3) to control the electrolyte level of the dialysate. The accuracy of the electrolytes concentration of the dialysate is however generally based on the accuracy of the pump (15) and/or on the accuracy of an optional scale (12) rather than on the conductivity sensor which serves only as a security means.

Monitoring the Water Content of the Patient

During the treatment, the system has to monitor the water content of the patient because an excessive amount of water should not be removed from the patient. Furthermore, the speed at which the water is removed may be also monitored. Thus, the system comprises means for controlling the removed water and the speed at which it is removed or has been removed.

The devices of the prior art use two distinct bags with dedicated scale, the first bag contains the fresh dialysate and the second bag contains the ultrafiltrate removed during the treatment. Thus, for monitoring the water content of the patient this device compares the amounts of each bags (first bag before the treatment and second bag after the treatment). Two major drawbacks appear: both scales have to be correctly calibrated and need to have a very good accuracy (but it is very difficult when each bag weighs more than 60 kg). In some cases, both bags are on the same scale, but the total weight is too high to ensure an accurate measurement for small quantities which need to be corrected in the patient fluid balance.

Our device uses only one bag in which the dialysate solution and ultrafiltrate removed during the treatment are stored. Indeed, since the system works in a loop circuit, a single scale (for example connected to the processor of the system) can be used to monitor the water content of the patient. If at the beginning of the treatment, the bag weighs 1 kg and after the treatment the bag weighs 1.2 kg, then the device has removed 0.2 kg of water. In such event, a certain amount of water can be re-injected into the patient via back-filtration and/or pre and/or post filtration (such as in a CRRT mode). The device of the invention has not the drawback of scale calibration because the system just monitors the differential of amount over time during the treatment so that the exact weight is not necessary (as in conventional systems with two scales).

In one embodiment, the system comprises a supply bag containing a fresh solution. In this case before to start the treatment all or a part of the solution contained in this supply bag is convey to the mixing bag which uses the single scale of the system. After this step, the weight of the solution stored in the mixing bag may be monitored so as to monitor the water content of the patient.

Furthermore, our device does not need a lot of fresh dialysate because the dialysate solution is regenerated during the treatment, and our scale can therefore be more accuracy. After a regeneration phase, if the system has injected 0.1 kg of additive (e.g. concentrate solution) in the bag, the new reference measurement is the last reference measurement to which the 0.1 kg will be added. In other terms, since the system works in a loop circuit (as a closed loop circuit), where the same fluid is regenerated, it is easy to balance the fluid in and out from the patient while limiting the risk of patient over or under fill which would require sophisticated method to prevent harmful potential circumstances.

The system preferably monitors the variation of the water content of the patient during the entire treatment and ensures a progressive removal of ultrafiltrate from the patient. In this case, the system may use the processor so as to switch the treatment mode. Further, since the system comprises a loop circuit, it is more secured against high variations of body fluid on the patient side (thanks to the weight scale), while reducing the septic contamination risks.

Pumping Means and Valve

The pumping means may be a unidirectional pump which may be a peristaltic pump.

The pump (21) may be adapted to pump solely or in combination the dialysate solution and the regeneration solution. Thus, the fluid distribution system may comprise at least one valve to select the solution to be moved.

Said at least one valve may be a proportional valve so that the system can pump at same time both solutions and the proportional valve commands the ratio dialysate/regeneration. The fluid distribution system shown in FIG. 6 may be adapted to use a proportional valve (or any other device having the same effect). Indeed, the spent dialysate solution which comes back from the filtration means can be pulled by a pump in such a way as to reach the sorbent device (23) then to reach the pump which may pump at same time a regeneration solution (in a proportional way) so that the mixed solution (regenerated dialysate solution) can be pushed by the pump (21) and reach the filtration means (25) via the first line. A mixing bag may be placed between the pump and the filtration means or between the sorbent device and the pump.

Embodiments Shown in FIGS. 1, 2 and 3

A dialysis solution flows from a bag to the filtration means and/or vice versa. In FIG. 1, the bag 3, 5 or 6 may store a fresh dialysate before starting the treatment or a saline solution. After a priming phase, the treatment can start. As a first step, a dialysis solution is taken in a bag, the pumping means (15) moves the dialysis solution to a filtration means (2). Then, the dialysis solution is removed from the filtration means (2), this dialysis solution is spent and can be named spent dialysis solution. The spent dialysis solution flows into the dialysate circuit to a sorption unit (8). Thanks to the sorption unit (8), the spent dialysis solution is converted into a semi-regenerated dialysis solution and it may be stored in the bag (3). The semi-regenerated dialysis solution may be used immediately so the dialysis solution of the bag 3 is conveyed a second time to the filtration means (2). Some time, the semi-regenerated dialysis solution needs to be blended with a volume fraction of a regeneration solution. Said regeneration solution may be calcium, magnesium and/or potassium (or other components). Thus, a volume fraction of the regeneration solution is pumped (via the pump used to move the dialysate) from the bag (4) as necessary to replenish ions that are removed via the sorption unit. This volume fraction is infused in the dialysate circuit; preferably the volume fraction is blended with the regenerated dialysate into the bag (3).

The FIGS. 1, 2 and 3, show three distinct embodiments but having the same first fluidic pathway (16) and the same third fluidic pathway. Indeed, the filtration means (2), the bag 4 and the pumping means (15) are fluidly connected via a fluidic pathway (16), optionally the bag (5) may be also fluidly connected to the same fluidic pathway (16). The bag 4 and 5 may store a dialysis solution or a regeneration solution or other fluid. One or more valves may be located in the fluidic pathway in such a way as to open or close the fluid communication between the elements (filtration, means, bag(s), pump . . . ). The third fluidic pathway (18) fluidly connects the bag (3) to the filtration means (2). Preferably, the outlet of the bag (3) is fluidly connected to the inlet of the filtration means (2). A valve (9) may be located between the filtration mans (2) and the bag (3).

Optionally, the third fluidic pathway (18) and the first fluidic pathway (16) are connected via a valve (9) (i.e. a single valve or an additional fluidic pathway comprising a valve) named recirculation valve. It's particularly useful for different reasons, for instance if the solution (which flows in the third channel) is too hoot or not good to be used, this solution may be deviated into the first fluidic pathway. Furthermore, if a regenerated solution is not homogeneously blended with a dialysis solution, the recirculation valve may be used to improve the mixing (e.g. if the conductivity measured is not appropriate). Furthermore, if too much regeneration solution has been injected into the bag 3, a volume fraction of the regenerated solution (of bag 3) can flow through the sorbent device in order to improve the mixing.

Referring now to FIG. 1, the second fluidic pathway fluidly connects the pumping means and the sorption unit (e.g. sorbent cartridge). The bag (3) is connected to the pump (15) directly (i.e. via a fluidic pathway, in particular the second fluidic pathway) or via the sorption unit. Thus, the pumped fluid can flow through the sorption unit (8) until the bag (3) or reach directly the bag without passing through the sorption unit (8). The controller may command the valve (9) in such a way to convey the fluid directly to the bag (3) or via the sorption unit (8).

The second fluidic pathway may also extend to an additional bag (6) in which a solution (for example the Ultra filtrate) may be stored during the treatment. The system may comprise a scale (not shown) in order to measure, compute and/or estimate the volume of removed ultrafiltrate which is store in the bag 6 and/or 3.

Referring now to FIG. 2, the additional bag (6) is withdrawn; the second fluidic pathway is connected from the pump (15) to the sorption unit (8), optionally to the bag (3) and/or optionally to the third fluidic pathway (18). Thus, the fluid can:

flow through the sorption unit (8) to remove some impurity and then reach the bag (3). The bag (3) being connected to the filtration means via the third fluidic pathway, the fluid, which is stored in the bag (3) can reach the filtration means (2).

reach directly the bag (3) without passing by the sorption unit (18) as disclosed above in the FIG. 1. Thus the sorption unit is bypassed. For example, if the bag (5) stores a fresh dialysate, the fresh dialysate can flow from the bag (5) to the bag (3). Indeed, the sorption unit (8) can alter, in whole or in part, the dialysate so it would be preferable to bypass the sorption unit (8).

reach directly the third fluidic pathway (18) without passing through the sorption unit (18) nor by the bag (3). For example for priming or cleaning . . . .

Referring now to FIG. 3, the fluid distribution system comprises a heater (7) to heat the fluid. The second fluidic pathway (17) conveys the fluid from the pump to the sorption unit (8), optionally directly to the heater (7) or optionally directly to the bag (3). An additional fluidic pathway may connect an outlet of the sorption unit (8) to an inlet of the heater (7) or to the second fluidic pathway between an inlet of the heater and a valve (the valve of the second fluidic pathway which connects the second fluidic pathway to the heater (7)). Another additional fluidic pathway may connect an outlet of the heater (7) to an inlet of the bag (3) or to the second fluidic pathway between an inlet of the bag (3) and a valve (the valve of the second fluidic pathway which connects the second fluidic pathway to the bag (3)).

The heater can be located upstream of the sorption unit or downstream of the bag (3) or can be arranged in a cassette (if the fluid distribution system comprises a cassette) or in the bag (3).

Phases of Use

During treatment a succession of phases may be performed:
Diffusion phase
Ultrafiltration phase
Dialysate recombination phase These phases described below are adapted for a system using a single pump in the dialysate circuit. However the same principle may be used with the system described in this document which uses two pumps in the dialysate circuit.

Although we distinguish the different phases of essentially Diffusion and Ultrafiltration, it is to be noted that Diffusion may also comprise some part of hemofiltration and/or ultrafiltration and Ultrafiltration phase may also comprise some part of Diffusion.

The FIGS. 8, 9 and 10 are different embodiments a part of a dialysis system of which the dialysate circuit which comprises a cassette (14) or a larger cassette (14').

Each embodiment (of the FIGS. 8, 9 and 10) comprises a cassette (14, 14') having valves (9) and at least one connection port intended to be connected to a filtration means (2), a first supply bag (4) for storing a regeneration solution, a single pumping means (15) which may convey a dialysis solution, a sorption unit (8) and a second bag (3).

The cassette (14, 14') may comprise:
- A first channel having two connection ports (which may externally extending from the cassette), of which one connection port intended to be connected to the first supply bag, and one connection port intended to be connected to the filtration means,
- A second channel having a connection port (which may externally extending from the cassette) intended to be connected to the sorption unit (8), and
- A third channel having two connection ports (which may externally extending from the cassette), of which one connection port intended to be connected to the second bag (3) and one connection port intended to be connected to the filtration means (2).

Preferentially, the first channel and the second channel are connected to said single pumping means (15) and the single pumping means (15) is operable to convey the dialysis solution from the filtration means to the sorption unit and the regeneration solution from the first bag (4) to the second bag (3).

The pumping means (15) may be arranged into the cassette (14, 14'). The system may comprise a heater to heat a dialysate solution. Said heater may be arranged inside the cassette. If the heater is outside of the cassette, the cassette may comprises at least one connection port which externally extends from the cassette, said connection port may be intended to be connected to an inlet and/or outlet of the heater. The heater may be arranged into the bag (3).

The system may comprise sensors (air sensor, pressure sensor, ammonia sensor, scale . . . ) to monitor the treatment. At least one sensor may co-operate with the cassette. In particular the system may comprise a conductivity sensor for monitoring the dialysis solution which flows through the system.

The embodiment of the FIG. 9 discloses two by-pass means. The first one is the by-pass which allows bypassing the sorption unit and/or the heater. Said by-pass means is arranged in the second channel and comprises valves which allow or not the communication to the sorption unit (8), heater (7) and/or by the bag (3). The second by-pass means is represented by a fluid passageway between the first channel and the third channel. Said fluid passageway is commanded by the recirculation valve, which may limit the channels.

Diffusion Phase

Referring now to FIGS. 8 and 9, during this phase the patient is actually treated based on a principle of diffusion (hemodialysis and/or hemofiltration). The dialysate circulates through the filtration means (2) pumped by the pump (15) from the mixing bag (so called second bag (3)). The dialysate may also be pulled from the filtration means (2) in such a way as to perform in part a convective clearance at the same time (hemofiltration). The used dialysate is pushed into the sorption unit (8) that will remove toxins but also some components of the dialysate (such as Calcium and Magnesium). The fluid may go then into a heater (7) to maintain the temperature of the dialysate in order to warm-up the blood when passing through the dialyser. A temperature of the dialysate near the body temperature prevents the cooling of the blood in the extracorporal system. A solution (e.g. a regeneration solution) may be then added in the mixing bag (3) that contains already a certain amount of dialysate. To create this circuit, the valve 1, 5 and 7 are opened (and 9 for the FIG. 9). Typically the regeneration solution may contain Calcium, Magnesium and other components.

The pressures may be monitored with sensors (10) before and after the pump (15) and also between the mixing bag (3) and the filtration means (2). These pressure sensors are used to detect occlusion.

The fluid temperature may be measured before and after the heater (2) for regulation. Like the dialysate that flows into the filter from the mixing bag (2), the temperature of the dialysate in this mixing bag (3) is measured by two distinct temperature sensors. Both measurements ensure the required safety in case of failure of one sensor.

During this phase, the scale (12) may monitor the mixing bag (3) weight and measures the ultra-filtrate (UF) extracted. The UF is extracted by the diffusion process, but also by the pressure difference through the membrane of the filter (transmembrane pressure) by principle of convection (hemofiltration). This pressure is created by the flow resulting from the pressure differential between the dialysate side and of the blood side. Ultrafiltration is used therefore to define the amount of fluid extracted from the patient by both diffusion and convection.

Ultrafiltration Phase

The UF obtained during the diffusion phases is maybe not sufficient to reach the required value. To obtain the required volume, another phase, dedicated more specifically to the UF extraction can optionally be performed. The principle used in this phase is convection by creating negative pressure with the pump on the dialysate side of the filter (e.g. by sucking with the pump from the dialysate outlet of the filter, applying a negative pressure on the dialysate side of the filter).

During this phase, the flow of dialysate through the filtration means (8) is interrupted, blocked by closing the valve 7. Only the valves 1 and 5 (and 9 for the FIG. 9) are opened and the pump (15) extracts the UF from the filtration means (8) by applying a negative pressure on the filter dialysate side. The extracted volume can be measured by the scale (12). The pressures may be monitored with sensors before and after the pump. The ammonia sensor may control the proper functioning of the sorbent. The temperatures may be measured by the same way than during the diffusion phase but with an adapted heating control according to the extracted volume considered.

It is to be noted that, in most of the cases, a combination of both Diffusion and Convection can be obtained in each of the Diffusion and Convection modes, although the proportion of each may be different.

Dialysate Recombination Phase

During the filtration phase, the solution coming from the mixing bag (3) may not be regenerated in an ideal way (lack of certain electrolytes because of the sorption process). This may not represent a problem as long as the concentration is not excessively effected (the larger the amount of fluid in the mixing bag, the lesser the problem). When such concentration may not be sufficient, a regeneration cycle shall be implemented.

During this regeneration phase, the flow of dialysate through the filtration means (2) is interrupted. The valve 2 and 6 are opened, a solution (regeneration solution) that contains the required electrolytes at a high concentration level is pumped to the heater (7) and then in the mixing bag (3). According to the FIG. 9, the regeneration solution may bypass the heater to increase the accuracy of the injected regeneration solution, in which case the valves 2 and 8 are opened. The resulting concentration of the dialysate electrolyte is driven by the volume of depleted dialysate pumped in the mixing bag (3) (measured by the dialysate pump during the diffusion phase), by the volume of concentrate (measured by the scale during this present phase) and by the accuracy of the concentration of the electrolytes in the initial dialysate and in the concentrate.

During the next phase following this recombination phase, a small amount of fluid may be pumped with the valve 6 opened and the valve 5 closed to flush the concentrate and prevent the concentrate to enter in the sorption unit.

The pressures may be monitored with sensors before and after the pump to detect occlusion. The temperatures may be measured by the same way than during the diffusion phase but with an adapted heating control according to the recombination volume considered.

Alternating Phases

The end of the treatment may be depending on the amount of removed ultra-filtrate. Thus, the aim of the system may be to reach a required amount of ultra-filtrate which may be determined by a caregiver over the therapy.

As disclosed above, during the diffusion phase the system removes some ultra-filtrate, but sometime this phase cannot reach the required value. Thus, the system may be adapted to switch between at least one diffusion phase and at least one ultrafiltration phase in such a way as to reach the determined amount of ultra-filtrate. One or more regeneration phase may be also performed during this treatment. This method of alternating phases is due to the design of the system which comprises only one pump for conveying a dialysate solution and the ultra-filtrate. It is also preferably to remove the ultra-filtrate progressively, to avoid patient blood pressure drop, during the entire treatment time.

Thus, the hemodialysis system is adapted to start a diffusion phase and after a determined time or depending on the amount of removed ultra-filtrate, the system stops the diffusion phase (prevents the dialysate solution to reach the dialyzer, for example, closing the valve 7) in such a way to perform an ultrafiltration phase (which may also include hemofiltration). The system may switch between this both phases on a determined frequency. The frequency may be computed or suggested by the system or determined by a caregiver. The frequency may depend on the determined amount of removed ultra-filtrate and/or on the water content of the patient, the duration of the treatment as well as the patient blood pressure may be also monitored during the treatment.

In one embodiment, to know the amount of the removed ultra-filtrate, the system comprises a scale which measures the solution amount contained in the mixing bag (3). The scale may be wirelessly connected to the processor of the system (or by cable). During the diffusion phase, the mixing bag stores a dialysate solution and the removed ultra-filtrate. While during the ultrafiltration phase, the removed solution is substantially the ultra-filtrate which may be stored in the mixing bag. The system is adapted to compute the ultra-filtrate during both phases. The system measures the solution stored in the mixing bag and computes the total amount of removed ultra-filtrate. When the total amount of removed ultra-filtrate is equal to the required value at a certain time of the therapy, the system may stop the process.

The electronic processor may be adapted to compute the time of each phase and the sequence of phases, for example using a mathematical model which takes account the UF or the data sent by sensor for example the scale of the mixing bag, the conductivity sensor, . . . .

In one embodiment which is not show by the figures, a determined amount of a dialysate solution may also be injected into the blood line directly before or after the filtration means, named respectively pre and post dilution. In this embodiment, a second pump may be located between the blood line and the dialysate line. Said pump is operable to inject dialysate solution into the blood line before and/or after the filtration means during a specific phase or during the diffusion phase or during the ultrafiltration phase. This is usually called CRRT, although in the embodiment of the invention this can be done with only 2 pumps on the dialysate side, versus 3 pumps in conventional systems. Such a system is particularly used in Intensive Care where the treatment can be maintained for a longer period of time or even continuously for several days.

Embodiments Shown in the FIGS. 11, 12, 15, 16, 17

A system with only one pump in the dialysate circuit favors a convective clearance. In certain circumstances, it may be preferable to combine convection and hemodialysis, as well as hemo-diafiltration, in order to improve the elimination of certain toxins from the blood. Thus, if the treatment needs to perform more diffusive clearance, the system can comprise an additional pump in the dialysate circuit.

A first pump can pull the dialysate solution from the filtration means, thus said pump may be arranged downstream the filtration means so as to favor the convective clearance. In other terms, the first pump creates a relative negative pressure at the outlet of the filtration means and a relative positive pressure at the inlet of the sorbent.

And, a second pump can push the dialysate solution to the filtration means, thus said pump may be arranged upstream the filtration means so as to favor the diffusive clearance. In other terms, the second pump creates a relative negative pressure at the outlet of the mixing bag and a relative positive pressure at the inlet of the filtration means.

Thus, the system may control the difference of pressure in the filtration means (dialyzer) between the blood side and the dialysate side thanks to the pumps. If the pressure of the dialysate side is smaller than the pressure of the blood side then the system favors a hemofiltration mode or ultrafiltration mode. If the pressure of the dialysate side is substantially equal to the blood side then the system favors a hemodialysis mode. If the pressure of the dialysate side is greater than the blood side then the system favors a back filtration mode. Thus for example, if the first pump creates a flowrate which is less important than the flowrate created by the second pump, the pressure of the dialysate solution downstream the second pump and upstream the first pump (for example the pressure of the dialysate side of the dialyzer) may be greater than the pressure of the blood side of the dialyzer, this operating mode of the system may favor a backfiltration.

The embodiments of FIGS. 11 to 17 show a system comprising two distinct pumps. The figures describe quasi-similar embodiments. The difference therebetween is the location of the supply bag (5) which is arranged in a same fluid pathway of one outlet of the filtration means (2) in the FIGS. 11 and 16 or in a same fluid pathway of one outlet of the supply bag (4) (concentrate supply bag) in the FIGS. 12, 15 and 17. Preferentially, the supply bag (5) contains a dialysate solution; nevertheless, it would contain other solution. If the system does not comprise a supply bag (5) containing a dialysate solution, the mixing bag (3) may be also used as a dialysate supply bag.

In the FIGS. 11 and 16, the first pump (15, 104) moves a solution from the filtration means (2, 105) or from the dialysate supply bag (5, 111) to the sorbent device (8, 106) or to the heater means (7, 107) or to the mixing bag (3, 108).

In the FIGS. 12, 15 and 17, the pump (15) moves a solution only from the filtration means. And, the pump (15') moves a solution from the supply bags (4, 5) or from the mixing bag (3) to the filtration means (2) or to the sorbent device (8, 106) or to the heater means (7, 107) or to the mixing bag (3, 108).

As explained above, the FIGS. 13 and 14 are a schematic view of the dialysate circuit. The main circuit is the full line while other line may be a bypass means.

The FIG. 17 shows a fluid distribution system (200) comprising a cassette (200') in which the channel of the cassette forms a part of the dialysate circuit. In particular, the cassette comprises two distinct channels (201, 202) separated by a pump (203). The first channel is connected to:
The second pump (203) (preferentially an inlet)
An inlet of a mixing bag (208), via a connection port and with a dedicated valve;
An inlet of a concentrate supply bag (210), via a connection port and with a dedicated valve;
Optionally, an inlet of a dialysate supply bag (211), via a connection port and with a dedicated valve;
The second channel is connected to:
The second pump (203) (preferentially an outlet)
An inlet of a dialyzer (205), via a connection port and with a dedicated valve;
An inlet of the mixing bag (208), via a connection port and with a dedicated valve;
Optionally, an inlet of a sorbent device (206), via a connection port and with a dedicated valve;
Optionally, an inlet of an heater means (207), via a connection port and with a dedicated valve;

The cassette comprises valves means illustrated by white circle. The system may comprise an electronic weigh balance (209) so as to monitor the volume of the fluid contained in the mixing bag (208).

Phases of Use

During a dialysis treatment, the system removes a determined amount of ultrafiltrate but some elements (such as water) should not be removed beyond a certain speed. Thus, the system is designed to control the treatment and perform different operating mode: ultrafiltration mode (or convective mode) and/or diffusion mode. During the treatment the system can change the mode in such a way to perform one or more phases which may be ultrafiltration phase, diffusion phase or regeneration phase. Preferably each of such phases shall be alternated in order to maintain a physiological blood pressure on the patient side (so as to avoid modifying the patient blood water content too rapidly over time).

Priming Mode

In the FIGS. 11 and 16, during a priming phase, the first pump (15, 104) pumps a solution from the supply bag (5, 111) so as to prime the dialysate circuit. If the solution contained in the supply bag (5, 111) is a ready to use dialysate, the solution is moved by the first pump (15, 104) until the mixing bag (3, 108). Preferentially, the major volume of the solution bypasses the sorbent device (15). Thus, the valves V3, V9 and V6 may be open. Optionally, before to reach the mixing bag, the solution may flows through the heating means (7) to heat at a determined temperature the solution. Thus, the valve V6 may be closed but the valve V8 and V7 are open. If the solution contained in the supply bag (5) is not a ready to use dialysate, the solution can first flow through the sorbent device (8) before reaching the mixing bag. Thus, the valves V7 and V3 are open and the valves V9, V8 and V6 may be closed.

In the FIGS. 12, 15 and 17, during the priming, the valve V3 is open, the second pump (15', 103) pumps the solution initially kept in the supply bag (5, 111) until the determined fraction volume of the solution has been reach in the mixing bag (3, 108). With a ready to use dialysate, the valve V9 is optional and closed, the valve V6 may be open and/or the valves V7 and V8 may be both open. With a dialysate not ready to use, the valves V7 and V9 are open and the valves V6 and V8 may be closed.

Hemodialysis Mode

In the FIGS. 15 and 17, during the hemodialysis mode, the second pump (103, 203) pulls the dialysate solution contained in the mixing bag. Said second pump is controlled by an electronic processor to pump at a determined speed for moving the dialysate solution to a predetermined flowrate called Qd. The pressures sensors arranged downstream and upstream the second pump monitor the treatment (for example the flow rate, . . . ). The valves V1 and V5 are open in such a way that the dialysate solution reaches the filtration means (105, 205).

The first pump (104, 204) pulls the dialysate solution (which is spent) from the filtration means (105, 205) at a predetermined flowrate (Quf+Qd). Indeed, the first pump pulls a dialysate solution which comprises the ultrafiltrate (resulting from the treatment). Thanks to the first pump, the dialysate solution first flows through the sorbent device (106, 206) and reaches the mixing bag (108, 208). The valve V7 is open. Optionally, before reaching the mixing bag (108, 208) the dialysate solution flows through a heater means (107, 207).

Reconstitution Mode

The system comprises a conductivity sensor arranged in the fluid pathway near an outlet of the mixing bag. Said sensor sends data to the processor about the quality of the dialysate solution. When the chemical property of the dialysate solution reaches a threshold, the system is adapted to change the operating mode so as to regenerate the dialysate solution.

During the reconstitution mode, the first pump (104, 204) may be stopped by the system while the second pump (103, 203) conveys the concentrate solution to the mixing bag (108, 208). The valves V2 and V6 (or v2, V7 and V8) are open. The second pump (103, 203) moves a determined fraction volume of the concentrate solution (initially kept in the concentrate supply bag (110, 210)). For monitoring the volume injected of the concentrate solution, the processor may control the second pump (for example the processor may count the number of strokes) or may monitor the data sent by the electronic weigh balance (109, 209). Both methods may be used for more security. Thus, the processor can compute or estimate the fraction volume of concentrate solution injected into the mixing bag.

At the end of the reconstitution mode, the second pump (103, 203) may be activated in such a way to move some dialysate solution (from the mixing bag) through the fluid pathway containing a residual concentrate solution. The processor may take account said residual concentrate solution in the total concentrate solution used for regenerating the dialysate solution. If necessary, the second pump can be activated until obtaining a homogeneous dialysate solution. The processor may use the data sent by the conductivity sensor to monitor said a homogeneous dialysate solution.

Hemofiltration Mode

In certain circumstances, it may be preferable to favor a convection clearance, for example to remove a determined volume of water from the patient. In this case, the second pump may be stopped. The valves V4 and V7 are open.

Other Operating Modes

During an ultrafiltration mode, the valve V4 and V5 may be closed and the first pump (104, 204) is activated.

To reduce the time of the treatment, it would be possible to perform all or a part of the reconstitution mode during a hemofiltration mode or ultrafiltration mode. Thus, the first pump (104, 204) is used for the treatment while the second pumps (103, 203) used for regenerating the dialysate solution. The valve V7 (optionally V4) is open for the treatment while the valves V2 and V6 (or V2, V6 and V7) are open for the reconstitution mode. The valve V1 may be open at the end of the reconstitution mode to move the residual concentrate solution contained in the fluid pathway.

To reduce the risk, the hemofiltration mode or ultrafiltration mode may be start at the end of the reconstitution mode for example when the dialysate solution is used to move the residual concentrate solution contained in the fluid pathway.

During the treatment, in certain circumstances, a fraction volume of a solution may be injected into the blood line (before or after the dialyzer). Thus, the first pump is used for the treatment while the second pumps used for injected a dialysate solution (or other solution initially kept in a supply bag) into the blood line. In this case, the fluid circuit comprise a fluidic pathway between the dialysate circuit and the blood circuit with a dedicated valve.

Control of the Flowrate

The system may control, via the first and the second pump, the flowrate upstream (Qd) and downstream (Qd+Quf) the dialyzer in such a way as to perform:

A hemodialysis mode, in this case, the Quf has to be small for example if Quf corresponds to an ultrafiltrate substantially equal to 2 liters per treatment or less A hemofiltration mode or ultrafiltration mode, in this case, the Quf has to be more important than the Quf of the hemodialysis, for example if Quf corresponds to remove more than 2 liters of ultrafiltrate per treatment;

A backfiltration mode, in this case, the Quf has to be <0 up to no flow with filtration pump.

In particular, as described above, to favor a mode, the system has to create a pressure differential between the dialysate side and the blood side in the dialyzer. Thus for a determined speed (or flowrate) of the blood pump:

if the treatment has to favor a hemofiltration mode or a hemo-diafiltration mode then the system has to control the dialysate pumps in such a way as to obtain an important pressure differential and thus an important Quf, for example with a speed of the second pump equal to Vuf;

if the treatment has to favor a hemodialysis mode then the system has to control the dialysate pumps in such a way as to obtain a Quf which is less important than the Quf of a hemo-diafiltration mode or a hemofiltration mode, for example with a speed of the second pump equal to Vh;

if the treatment has to favor a backfiltration mode then the system has to control the dialysate pumps in such a way as to obtain a Quf close to 0, for example with a speed of the second pump is equal to Vb.

Thus, Vuf>Vh>Vb wherein the Vb is close to 0

Examples of Systems or Methods of the Invention

In one possible embodiment, the dialysis system comprises:

A cassette having valves and at least one connection port;
A first supply bag for storing a regeneration solution;
A single pumping means;
A sorption unit;
A second bag;

The cassette may comprise:

A first channel having two connection ports, of which one connection port intended to be connected to the first supply bag, and one connection port intended to be connected to a filtration means A second channel having a connection port intended to be connected to the sorption unit (8)

A third channel having two connection ports, of which one connection port intended to be connected to the second bag and one connection port intended to be connected to the filtration means;

The first channel and the second channel are connected to the single pumping means which is operable to convey the dialysis solution from the filtration means to the sorption unit and the regeneration solution from the first bag to the second bag. The second channel may have an additional connection port intended to be connected to the second bag which may store a dialysis solution.

The cassette and the single pumping means may be operable to remove a dialysis solution from the filtration means, to convey this dialysis solution through the sorption unit until the second bag. The cassette may comprise a channel which connected fluidly the sorption unit to the second bag.

The first channel may be connected to an inlet of the pumping means and the second channel is connected to an outlet of the pumping means.

The third channel may be connected to the first channel via an additional valve or may be connected to the second channel via a valve.

The first channel may comprise an additional connection port with a dedicated valve, intended to be connected to a third bag which may contain a fresh dialysis solution.

The system may comprise a fourth bag for storing a spent dialysis solution or a solution used to clean the sorption unit.

Preferentially, the system may comprise a scale so as to monitor only the weight or the volume of the fluid contained in the second bag and/or in the fourth bag.

The second bag may comprise a fresh dialysis solution before starting the treatment and/or is used as a buffer bag during the treatment and/or is used as a mixing bag in which the regeneration solution is blended with the dialysate which has flowed through the sorption unit.

The filtration means may be a dialyzer having an inlet connected to the first channel and an outlet connected to the third channel. In this case, the cassette may comprise at least another channel wherein the blood of patient flows. In other embodiment, the filtration means may be a peritoneal cavity of a patient.

The scale and/or the pumping means may be used for monitoring the change in water content of the patient over the treatment.

In another embodiment, the system is adapted to perform kidney replacement treatment, said system comprise:
  a regeneration solution being stored in a first supply bag,
  a dialysate circuit having a main closed line, at least one valve and at least one pump for conveying a dialysis solution through a filtration means and a sorbent,
  a means for regenerating dialysis solution which has flowed through the sorbent.

One pump is operable to convey the regeneration solution from the first supply bag into the dialysate circuit and the dialysate solution into the main closed line.

The system may comprise a cassette which includes at least a part of the dialysate circuit.

The means for regenerating dialysis solution may comprise a mixing bag in which the regeneration solution is blended with the dialysis solution which has flowed through the sorbent. Furthermore, the mixing bag may be adapted to trap the air of the dialysate circuit.

The mixing bag may be monitored by a scale to measure, compute or estimate the fluid balance from the patient, for instance the change in water content of the patient over the treatment.

The system may be configured to take into account the amount of regeneration solution injected into the mixing bag.

The dialysate circuit and one pump may be operable to remove a dialysis solution from the filtration means and to convey this dialysis solution through the sorbent cartridge to the mixing bag. The dialysate circuit and an additional pump may be operable to remove a dialysis solution from the mixing bag and to convey this dialysis solution through filtration means.

The dialysate circuit may comprise at least one by-pass means so that the pump is operable to convey a solution without flowing through the main closed line, e.g. through the filtration means and/or the sorbent cartridge. The system may comprise an automatic controller means for controlling the by-pass means depending on the fluid which is pumped.

In another embodiment, the system is adapted to regenerate a dialysis solution, said system comprises:
  A pumping means,
  A control means,
  A fluid distribution means for distributing a solution,
  A regenerating solution stored in a first bag,
  A sorbent cartridge for removing at least one impurity or waste from a dialysis solution,
  A mixing bag,
  The fluid distribution means comprises a fluidic pathway having at least two distinct ports so that the dialysis solution moves from the pumping means to a first or a second ports, wherein the first port with dedicated valves is connected to the sorbent cartridge and a second port with dedicated valves is connected to the mixing bag. The sorbent cartridge is also connected to the mixing bag via an additional fluidic pathway.

The fluid distribution means may be operable to convey a solution from the pumping means directly to the mixing bag or via the sorption unit.

The control means may be arranged to close said first port of channel when said second port is open and/or vice versa.

The control means may be arranged to open said first port of channel when said second port is closed.

The control means may be arranged to control the valves of said first and second port depending of the pumped solution.

The same pumping means may be arranged to pump the dialysis solution and the regeneration solution.

The control means may be adapted to close said first port and open said second port when the solution pumped is a regenerating solution, at least temporary.

The control means may be adapted to open said first port and close said second port when the solution pumped is a dialysis solution which has been spent, at least temporary.

In another embodiment, the cassette is adapted to distribute a fluid during a dialysis treatment, said cassette comprises:
  A first channel which has two distinct connection ports, of which one connection port, with dedicated valve means, being intended to be connected to an outlet of a filtration means and one connection port, with dedicated valve means, being intended to be connected to a first supply bag; said first channel being connected to an inlet of a pump;
  A second channel which has one connection port intended to be connected to a sorbent cartridge which is on fluid communication with an inlet of a second bag; said second channel may be connected to an outlet of the same pump;
  A third channel having at least one valve and two distinct connection ports, of which one connection port intended to be connected to an outlet of the second bag and of which one connection port intended to be connected to an inlet of the filtration means;

The first channel and the second channel are arranged to convey a dialysis solution from the filtration means to the second bag and to convey a solution from the first bag to the second bag.

The first and the third channel may be connected via a valve. And/or the second and the third channel may be connected via a valve.

The first bag may store a regeneration solution. The second bag may be used as a mixing bag in which the dialysate which has flowed through the sorbent cartridge is mixed with a regeneration solution. The cassette may be connected to an additional bag containing a fresh dialysate, wherein said additional bag is connected to the first channel with a dedicated port and an optional valve.

The second bag may comprise a scale which is used to measure precisely the actual balance of fluid, resulting from the amount of additional fluid coming from the patient and the dialysate fluid injected into the patient.

In another embodiment, a system is adapted to perform a hemodialysis treatment, said system comprises:
 A bag
 A scale adapted to measure an amount of solution stored in the bag
 A dialyzer
 Two distinct fluid passageway in which valves are arranged
 At least one pumping means adapted to move a solution through the fluid passageways
 A first fluid passageway is arranged to flow a solution from the bag to the dialyzer and a second fluid passageway is arranged to flow a solution from the dialyzer to the bag.

The system may comprise a processor adapted to command the valves and the at least one pumping means.

The processor may be arranged to open the valve and to actuate the pump in such a way to perform a diffusion phase. The processor may be arranged to close the valve and to actuate the pump in such a way to perform a ultrafiltration phase.

At least one pumping means may be arranged into the first fluid passageway and at least one pumping means may be arranged into the second fluid passageway The processor may be arranged to control the pumps and the valves so as to change an operating mode to favor a diffusive clearance, a convective clearance or a back filtration. The scale may be connected to the system and used by the processor so as to monitor the treatment. The processor may be adapted to determine, calculate or suggest the frequency of operating mode and control the system so as to reach the goal of the treatment.

In one embodiment, the dialysis system comprises a dialysate circuit in which a dialysate solution is moved by at least one pump, said dialysate circuit allows the dialysate solution to flow through a dialyzer so as to perform a dialysis treatment and through a sorbent device so as to remove some solute contained into the dialysate solution. The system further comprises a mixing bag, a regeneration supply bag containing a regeneration solution and an electronic processor. Preferentially, the dialysate circuit is a loop circuit comprising the mixing bag, the dialyzer, at least one pump and the sorbent device.

A pump may convey a dialysate solution through the dialysate circuit (which is a loop circuit) and the same pump may inject into said dialysate circuit another solution which may be a regeneration solution. Thus, at least one pump of the dialysate circuit may be arranged to pump the regeneration solution.

Preferentially, the regeneration solution may be moved from the regeneration supply bag into the mixing bag without passing through the dialyzer nor the sorbent device.

The system may comprise an electronic scale arranged to weigh the mixing bag. This scale may be a single scale or two redundant scales for the security.

Preferentially, the electronic scale weighs only the mixing bag, in particular to monitor the weight or the volume of the fluid contained into the mixing bag.

The electronic processor may receive the data of the scale and may use this data to compute or to estimate the amount of ultrafiltrate removed during the treatment and/or the amount of regeneration solution injected into the mixing bag.

The system may further comprise a cassette which may comprise channels forming a part of the dialysate circuit and valves controlled by the system.

The cassette may comprise a first channel which may be connected to an outlet of the mixing bag via a connection port and with a dedicated valve, to an outlet of the regeneration supply bag via a connection port and with a dedicated valve and optionally to an outlet of a dialysate supply bag via a connection port and with dedicated valve.

The cassette may comprise a second channel which may be in fluid communication with an inlet of the mixing bag and/or an inlet of a heater means and/or an inlet of the sorbent device.

The inlet of the mixing bag may be connected to the cassette via a connection port and with a dedicated valve.

The second channel may be connected to an inlet of the dialyzer via a connection port and with dedicated valve.

The processor may be arranged to close the valve of dialyzer connected to the second channel when the valve of the regeneration supply bag connected to the first channel is open. Said valves may be arranged in the cassette and may be actuated by an valve actuator connected to the processor of the system.

The system may comprise two distinct pumps into the dialysate circuit.

Preferentially, one pump may be arranged between one outlet of the mixing bag and one inlet of the dialyzer.

Preferentially, one pump may be arranged between one outlet of the dialyzer and one inlet of the sorbent device.

The electronic processor may be adapted to control and/or monitor the speed of each pump so as to favor a diffusive clearance or a convective clearance or a backfiltration. For example, the processor may use a mathematical model which computes the speed of each pump or the flowrate depending on the goal of the treatment and/or on the operating mode.

The electronic processor may be arranged to control the pressure in the filtration means of the dialysate side so as to favor a diffusive clearance or a convective clearance or a backfiltration. For example, the pumps (first pump, second pump of the dialysate circuit and/or the blood pump) may be used to create a differential pressure between the blood side and the dialysate side of the dialyzer. For example, a first pump may be located downstream the dialyzer, and a second pump may be located upstream the dialyzer, if the flowrate of the first pump is much greater than the second, then the system may favor a convective clearance; if the flowrate of the first pump is slightly greater than the second, then the system may favor a diffusive clearance; if the flowrate of the second pump is greater than or substantially equal to the first, then the system may favor a backfiltration (some solute of the dialysate may pass through the membrane of the dialyzer and thus may be injected into the blood of the patient).

The dialysate circuit may comprise at least one bypass. One bypass may allow a solution flowing through the dialysate circuit without passing through the sorbent device. One bypass allows a solution flowing through the dialysate circuit without passing through the filtration means. One bypass means allows a solution flowing through the dialysate circuit without passing through one of pump.

Each features described in this document may be comprise in one embodiment of the system.

In one embodiment, the system describes in this document may be used for performing a hemodialysis treatment, hemodiafiltration treatment, hemofiltration treatment and/or backfiltration.

The invention also describes:

a method for conducting a dialysis treatment, said method may comprise the following steps:
(i) conveying a dialysis solution into a dialyzer for performing the dialysis treatment;
(ii) withdrawing from the dialyzer the dialysis solution;
(iii) conveying the dialysis solution through a sorption unit to withdrawn impurity or waste from the dialysis solution which comes from the dialyzer;
(iv) conveying a regeneration solution from a first supply bag to a mixing bag containing the dialysis solution which has flowed through the sorption unit
(v) providing a pumping means to convey the dialysis solution and the regeneration solution a method for conducting a dialysis treatment, said method may comprise the following steps:
(i) Using a pump for conveying a dialysis solution into a dialyzer for performing the dialysis treatment;
(ii) Using the same pump for conveying the dialysis solution through a sorption unit to withdrawn impurity or waste from the dialysis solution which comes from the dialyzer;
(iii) Using the same pump for conveying a regeneration solution from a first supply bag to a mixing bag containing the dialysis solution which has flowed through the sorption unit A method for reaching a determined amount of removed ultra-filtrate and/or hemofiltrate during a hemodialysis and/or hemodialfiltration treatment, said method may comprise the following steps:
(i) Performing at least one diffusion phase;
(ii) Performing at least one ultrafiltration and/or hemodiafiltration phase;
(iii) Measuring the amount of the removed ultra-filtrate and/or hemofiltrate;

The number of each phase and/or the duration of each phase depends on the determined amount of removed ultra-filtrate and/or hemofiltrate.

In one embodiment, the method may comprise at least one phase of regeneration of a dialysate solution. The number of each phase and/or the duration of each phase may depend on a determined duration and/or sequence of the treatment. The method may be performing by a machine adapted to automatically compute and/or suggest the frequency of phases.

The method may be performing by a machine which comprise scale, wherein the measure of amount of the removed ultra-filtrate is perform by the scale which may be connected to the machine.

A method for performing a dialysis treatment, said method may comprise the following steps:
(i) Performing an operating mode which favors the diffusive clearance; and/or
(ii) Performing an operating mode which favors the convective clearance; and/or
(iii) Measuring the amount of the ultrafiltrate removed from the patient;
(iv) Adjusting the flowrate of fluids to switch the operating mode depending on the measures of the ultrafiltration.

The invention claimed is:

1. A dialysis system comprising:
a blood circuit;
a dialysate loop circuit;
a dialyzer in fluid communication with the blood circuit and the dialysate loop circuit;
wherein the dialysate loop circuit includes,
a first container for mixing dialysis solution;
a sorbent device for providing regenerated dialysis solution, in fluid communication with the first container;
a first pumping device configured to move the dialysis solution from the first container to the dialyzer; and
a second pumping device configured to move a spent dialysis solution from the dialyzer to the first container by passing through the sorbent device such that the regenerated dialysis solution from the sorbent device is mixed with the dialysis solution located in the first container;
a controller; and
a second container for storing a regeneration solution and a fluidic pathway configured to inject the regeneration solution into the dialysate loop circuit,
wherein the controller is configured to operate the dialysis system according to (i) a hemodialysis mode operating the first and the second pumping device during which the dialysis solution from the first container and the spent dialysis solution from the dialyzer flow through the dialysate loop circuit, and (ii) an ultrafiltration mode during which the dialysis solution flow is stopped by either stopping the first pumping device or closing a valve in the dialysate loop circuit, while the spent dialysis solution flows from the dialyzer, through the sorbent to become the regenerated dialysis solution, and then reaches the first container, and the regeneration solution is injected into the dialysate loop circuit in order to reach the first container for mixing with the dialysis solution.

2. The dialysis system according to claim 1, further comprising:
a scale that monitors a scale weight of the fresh dialysate solution stored in the first container.

3. The dialysis system according to claim 2, wherein the controller is further configured to determine an amount of ultra-filtrate and/or of the regeneration solution in the first container in response to the scale weight of the dialysate fluid in the first container.

4. The dialysis system according to claim 2, wherein the controller is further configured to determine an amount of ultra-filtrate in the first container and to take into account the amount of regeneration solution added to the dialysate loop circuit.

5. The dialysis system according to claim 1, wherein the first container is configured to receive gas which flows in the dialysate loop circuit.

6. The dialysis system according to claim 1, wherein the first container includes an outlet having an opening fully immerged in the dialysis solution.

7. The dialysis system according to claim 1, further comprising:
a first bypass device allowing the solution which flows through the dialysate loop circuit to bypass the sorbent device.

8. The dialysis system according to claim 7, further comprising:
a second bypass device allowing the solution which flows through the dialysate loop circuit to bypass the dialyzer.

9. The dialysis system according to claim 1, wherein the controller is configured to control the first pumping device and the second pumping device to favor a diffusive clearance or convective clearance.

10. The dialysis system according to claim 1, wherein the controller is configured to switch between the (i) hemodialysis mode and the (ii) ultrafiltration mode so as to reach a determined amount of ultra-filtrate removed from the patient.

11. The dialysis system according to claim 10, wherein the controller is configured to determine the mode depending on at least one of the amount of ultra-filtrate, a water content of the patient, a duration of the, and a blood pressure of the patient.

* * * * *